(12) United States Patent
Erickson et al.

(10) Patent No.: US 11,733,243 B2
(45) Date of Patent: Aug. 22, 2023

(54) USE OF ACAMPROSATE TO MODULATE ERK1/2 ACTIVATION IN ANIMAL MODELS FOR FXS AND ASD AND INDIVIDUALS DIAGNOSED WITH FXS AND ASD

(71) Applicant: Indiana University Research and Technology Corporation, Indianapolis, IN (US)

(72) Inventors: Craig Erickson, Wyoming, OH (US); Debomoy Lahiri, Brownsburg, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/818,854

(22) Filed: Mar. 13, 2020

(65) Prior Publication Data

US 2020/0225233 A1    Jul. 16, 2020

Related U.S. Application Data

(62) Division of application No. 15/029,596, filed as application No. PCT/US2014/060527 on Oct. 14, 2014, now Pat. No. 10,634,677.

(60) Provisional application No. 61/890,756, filed on Oct. 14, 2013.

(51) Int. Cl.
*A61K 31/185* (2006.01)
*G01N 33/573* (2006.01)
*A61K 31/16* (2006.01)

(52) U.S. Cl.
CPC ........... *G01N 33/573* (2013.01); *A61K 31/16* (2013.01); *A61K 31/185* (2013.01); *G01N 2333/4709* (2013.01); *G01N 2333/48* (2013.01); *G01N 2333/91205* (2013.01); *G01N 2500/20* (2013.01); *G01N 2800/2814* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,316,635 B1 | 11/2001 | Tang et al. |
| 6,593,133 B1 | 7/2003 | Johansen et al. |
| 7,354,939 B2 | 4/2008 | Martinez-Botella et al. |
| 8,008,539 B1 | 8/2011 | Tan et al. |
| 2007/0082366 A1 | 4/2007 | Khan et al. |
| 2008/0139472 A1 | 6/2008 | Lauterborn et al. |
| 2008/0227709 A1 | 9/2008 | Pascual et al. |
| 2009/0082464 A1 | 3/2009 | Jandeleit et al. |
| 2009/0239888 A1 | 9/2009 | Walter et al. |
| 2010/0029770 A1 | 2/2010 | Roberts et al. |
| 2010/0203044 A1 | 8/2010 | Nikolaev et al. |
| 2012/0016036 A1 | 1/2012 | Erickson |
| 2013/0052644 A1 | 2/2013 | Gomez-Mancilla et al. |
| 2016/0266120 A1 | 9/2016 | Erickson et al. |

FOREIGN PATENT DOCUMENTS

| | | |
|---|---|---|
| CA | 2671903 A1 | 7/2008 |
| EA | 0003734 B1 | 8/2003 |
| EA | 201370025 A1 | 8/2013 |
| EP | 2626352 A1 | 8/2013 |
| JP | 2012-517480 A | 8/2012 |
| RU | 2009128039 A | 1/2011 |
| UA | 84930 C2 | 12/2008 |
| WO | 97/33585 A1 | 9/1997 |
| WO | 00/01815 A2 | 1/2000 |
| WO | 01/12184 A1 | 2/2001 |
| WO | 2004/079371 A1 | 9/2004 |
| WO | 2005/113541 A1 | 12/2005 |
| WO | 2008/080045 A2 | 7/2008 |
| WO | 2010/093859 A1 | 8/2010 |
| WO | 2011/150380 A1 | 12/2011 |
| WO | 2012/024630 A1 | 2/2012 |
| WO | 2012/030258 A1 | 3/2012 |
| WO | 2014/018468 A1 | 1/2014 |

OTHER PUBLICATIONS

Busca et al (Frontiers in Cell and Developmental Biology 4:1-23, 2016) (Year: 2016).*
Caraglia et al (Cell Death and Disease 2:e150, 2011) (Year: 2011).*
Graf et al (Frontiers in Psychology 12: pp. 1-12, 2021) (Year: 2021).*
Cleveland Clinic (available online at https://my.clevelandclinic.org/health/diseases/5476-fragile-x-syndrome#symptoms-and-causes, accessed Apr. 20, 2022) (Year: 2022).*
Ray et al (PLoS One 6:1-10, 2011) (Year: 2011).*
Bailey A.R., "Peripheral biomarkers in Autism: secreted amyloid precursor protein-alpha as a probable key player in early diagnosis" International Journal of Clinical and Experimental Medicine, vol. 1, No. 4, Jan. 1, 2008 (Jan. 1, 2008); 7 pages.
Cheng et al (Exp Neurol 175:407-414, 2002).
Connolly et al., "Brain-Derived Neurotrophic Factor and autoantibodies to Neural Antigens in Sera of children with Autistic Spectrum Disorders Landau-Kleffner Syndrome and Epilepsy", Biological Psychiatry. Elsevier Science, New York, NY; US, vol. 59, No. 4, Feb. 15, 2006 (Feb. 15, 2006); 10 pages.

(Continued)

*Primary Examiner* — Craig D Ricci
(74) *Attorney, Agent, or Firm* — Faegre Drinker Biddle & Reath LLP

(57) ABSTRACT

Studies in mouse models of Fragile X and preliminary studies in human youth demonstrate that ERK1/2 is biomarker useful to monitoring the treatment of people diagnosed with ASD. Results reported herein demonstrate that acamprosate has the ability to reduce levels of ERK1/2 activation associated with many of the symptoms of ASD. Accordingly, in addition to its utility as a diagnostic marker for ASD ERK1/2 activation levels can be used to monitor patients treated with acamprosate and to screen potentially therapeutic compounds.

7 Claims, 5 Drawing Sheets

(56) References Cited

OTHER PUBLICATIONS

De Witte et al (CNS Drugs 19:517-537, 2005—Abstract only).
Erickson C.A. et al. "Brief Report: Acamprosate in Fragile X Syndrome", Journal of Autism and Developmental AL Disorders. Kluwer Academic Publishers—Plenum Publishers. NE, vol. 40, No. 11, Mar. 6, 2010 (Mar. 6, 2010); 5 pages.
Erickson, C.A. et al., "An Open-Label Naturalistic Pilot Study of Acamprosate in Youth with Autistic Disorder", Journal of Child and Adolescent Psychopharmacology, vol. 21, No. 6, Dec. 1, 2011 (Dec. 1, 2011); 5 pages.
Erickson, Craig A., et al., "Initial analysis of peripheral lymphocytic extracellular signal related kinase activation in autism." Journal of Psychiatric Research, vol. 84, (2017); pp. 153-160.
Erickson, Craig et al., Impact of acamprosate on behavior and brain-derived neurotrophic factor: an open-label study in youth with fragile X syndrome, Psychopharmacology, vol. 228, No. 1, Feb. 24, 2013; pp. 75-84.
Erickson, Craig et al., "Impact of acamprosate on plasma amyloid-(Beta) precursor protein in youth: A pilot analysis in fragile X syndrome-associated and idiopathic autism spectrum disorder suggests a pharmacodynamic protein marker," Journal of Psychiatric Research, vol. 59, Aug. 2014; pp. 220-228.
European Search Report and Search Opinion Received for EP Application No. 14854852.2, dated Mar. 22, 2017, 7 pages.
Extended European search report issued by the European Patent Office, dated Jul. 5, 2016, for European Application No. 13823641.9; 17 pages.
FDA—Guidance for Industry (Dosage and Administration Section of Labeling for Human Drug and Biological Products, Mar. 2010).
International Preliminary Report on Patentability issued by the International Bureau of WIPO, dated Apr. 19, 2016, for International Application No. PCT/US2014/060527; 15 pages.
International Preliminary Report on Patentability issued by the International Bureau of WIPO, dated Jan. 27, 2015, for International Application No. PCT/US2013/051550; 7 pages.
International Search Report and Written Opinion issued by the ISA/US Commission for Patents, dated Jan. 23, 2015, for International Application No. PCT/US2014/060527; 17 pages.
International Searching Authority, International Search Report and Written Opinion for PCT/US2013/051550, dated Nov. 8, 2013; 11 pages.
Jolly-Tornetta, et al., "Regulation of Amyloid Precursor Protein Secretion by Glutamate Receptors in Human Ntera 2 Neurons (NT2N)", The Journal of Biological Chemistry, vol. 273, No. 22, May 29, 1998; 8 pages.
Lahiri, Debomoy K., et al., "Autism as early neurodevelopmental disorder: evidence for an sAPPa-mediated anabolic pathway," Frontiers in Cellular Neuroscience, vol. 7, No. 94, Jun. 21, 2013; pp. 1-13.

Mann, Karl, et al., "Does Acamprosate Really Produce its Anti-Relapse Effects via Calcium? No Support from the PREDICT Study in Human Alcoholics," Neuropsychopharmacology, (2016), vol. 41; pp. 659-660.
Mebratu, Yohannes, et al., "How ERK1/2 Activation Controls Cell Proliferation and Cell Death Is Subcellular Localization the Answer?," NIH Public Access, Cell Cycle, Apr. 15, 2009, vol. 8, No. 8; 18 pages.
Pacheco, et al., "Group I Metabotropic Glutamate Receptors Mediate a Dual Role f Glutamate in T Cell Activation", The Journal of Biological Chemistry, vol. 279, No. 32, Aug. 6, 2004; 8 pages.
Partial supplementary European Search Report issued by the European Patent Office, dated Mar. 8, 2016, for European Application No. 13823641.9; 11 pages.
Politte, et al., "Phase II and III drugs for the treatment of fragile X syndrome", Expert Opinion on Orphan Drugs, 2013, 1:1, pp. 47-65.
Ray et al (PLoS One 6:1-10, 2011).
Reilly, Matthew T., et al., Effects of Acamprosate on Neuronal Receptors and Ion Channels Expressed in Xenopus Oocytes, Alcohol Clin Exp Res. Feb. 2008; 32(2): 188-196.doi: 10. 1111/j.1530-0277.2007.00569.x; 18 pages.
Retraction, Genes, Brain and Behavior, (2013). vol. 12; p. 593.
Sokol, et al., "Autism, Alzheimer disease, and fragile X; APP, FMRP, and mGluR5 are molecular links, "Neurology 76; pp. 1344-1352, 2011; 9 pages.
Spanagel, Rainer, et al., "Reply to: Does acamprosate really produce its anti-relapse effects via calcium? No support from the PREDICT study in human alcoholics," Neuropsychopharmacology (2016), vol. 41; pp. 661-662.
Spanagel, Rainer, et al.,"Acamprosate Produces Its Anti-Relapse Effects via Calcium," Neuropsychopharmacology (2014), vol. 39; pp. 783-791.
Wang, et al., "Activation of the extracellular signal-regulated kinase pathway contributes to the behavioral deficit of fragile x-syndrome", Journal of Neurochemistry, 2012, vol. 121; pp. 672-679.
Weng, Ning, et al., "Early-phase ERK Activation as a Biomarker for Metabolic Status in Fragile X Syndrome," American Journal of Medical Generics Part B (Neuropsychiatric Genetics), vol. 147B, No. 7, Oct. 5, 2008; pp. 1253-1257.
Westmark et al (PLoS Biol 5:629-639, 2007).
Yang, K., et al., "Upregulation of Ras/Raf/ERK1/2 signaling and ERK5 in the brain of autistic subjects," Genes, Brain and Behavior, (2011), vol. 10; pp. 834-843.
Zou, H., et al., "Association of upregulated Ras/Raf/ERK1/2 signaling with autism," Genes, Brain and Behavior, (2011), vol. 10; pp. 615-624.
Office Action issued by the Canadian Intellectual Property Office, dated Jan. 4, 2021, for Canadian Patent Application No. 2,926,645; 8 pages.
Office Action issued by the Canadian Intellectual Property Office, dated Aug. 25, 2021, for Canadian Patent Application No. 2,926,645; 5 pages.

* cited by examiner

USE OF ACAMPROSATE TO MODULATE ERK1/2 ACTIVATION IN ANIMAL MODELS FOR FXS AND ASD AND INDIVIDUALS DIAGNOSED WITH FXS AND ASD

CROSS REFERENCE TO RELATED APPLICATIONS

This application is a divisional of U.S. patent application Ser. No. 15/029,596, filed Apr. 14, 2016, now allowed, which is a U.S. National Phase filing of PCT/US14/60527, filed Oct. 14, 2014, which claims the benefit of U.S. Provisional Patent Application Ser. No. 61/890,756, filed Oct. 14, 2013, the contents of each of which are expressly incorporated by reference herein.

STATEMENT OF GOVERNMENT RIGHTS

This invention was made with government support under AG018379 and RR025761 awarded by the National Institutes of Health. The government has certain rights in the invention.

FIELD

Aspects of this disclosure relate to modulating the serum levels of proteins selected from the group consisting of: peripheral lymphocytic extracellular signal-related kinase (ERK1/2) activation, secreted amyloid precursor protein (sAPP); sAPPo; brain derived neurotrophic factor (BDNF) by the use of compounds such as acamprosate to treat patients diagnosed with specific developmental disorders selected from the group consisting of Fragile X Syndrome (FXS), FXS-related autistic spectrum disorder, and idiopathic autistic spectrum disorder (ASDs, autism).

BACKGROUND

The neurodevelopmental disorders autism spectrum disorders (ASDs: autism) and Fragile X Syndrome (FXS) are childhood lifelong disorders that may result in marked impairment in social behavior, communication skills, and cognitive function. The severity of the symptoms exhibited by individual identified with these neurodevelopmental disorders vary widely. Unfortunately, many individual afflicted with these disorders exhibit profound symptoms some are unable to care for themselves while other exhibit greatly diminished capacity to function in society. While the cause of FXS is known the various neuronal pathways afflicted by this condition is unknown as are the levels of specific neuroactive compounds in the brains of these individual. With regard of idiopathic autistic disorder even the root cause of the disorder remains unknown. Because of the impact that these disorders have on those diagnosed with the disorder there is an intense amount of pre-clinical and clinical research devoted to developing treatments for these conditions. Despite the work devoted to diagnosing and treating there remains a pressing need for new therapies to help individuals afflicted with these disorders lead more comfortable and independent lives. The materials, methods, and systems disclosed herein are intended to address these vital needs.

Autism spectrum disorders are lifelong childhood-onset neurodevelopmental disorders causing marked impairment in social behavior and communication. According to the Department of Health & Human Services (DHHS), the rising prevalence of ASDs, currently estimated at 1 in 110 children, warrants ASDs being considered a national health emergency. Persons with ASD also frequently exhibit additional interfering symptoms such as aggression, self-injury, compulsions, inattention, hyperactivity, and anxiety among others. The costs of ASDs (estimated at $95 billion annually in the United States) to society is large and ever increasing. The presentation of autism is heterogeneous. For example, persons with autism may or may not have intellectual disability, seizures, or functional speech. This heterogeneity has made both research into the cause and effective treatment of ASDs challenging. An understanding of the cause of autism remains elusive with only approximately 10% of cases being associated with known genetic abnormalities. Regarding treatment, to date no drugs have been shown effective in large-scale trials to treat the core social and communication impairments of ASDs. The heterogeneity of autism has led to many promising drug treatments failing large-scale trials due to difficulty identifying appropriate subgroups for testing. Given such variable presentation, rationale drug development in autism will need to focus on defining appropriate subgroups where drug benefit is maximized. Biomarker development in autism presents a unique opportunity to address these challenges of therapeutic development. The 2011 *Strategic Plan of the Department of Health & Human Services Interagency Autism Coordinating Committee* strongly emphasized the need for autism biomarker development given the potential of biomarkers to provide early disease detection, assessment of illness severity, indicators of pharmacological response, and the ability to utilize biomarkers to identify subgroups within autism for targeted treatment development.

Given the heterogeneity of autism, known causes of autism provide the best foundation for pharmacotherapy and biomarker development. Among these known causes, recent research findings in Fragile X Syndrome (FXS) combined with the status of FXS as the most common single gene cause of autism make this disorder a prime candidate upon which to develop an autism therapeutics development strategy. FXS is the most common inherited form of developmental delay impacting 1 in 4,000 persons. Two in three persons with FXS also suffer from autism and overall FXS accounts for 5-7% of all autism cases.

To date, no drug has been approved by the United States Food and Drug Administration (FDA) for reducing the core social impairment of autistic disorder. Many pharmacotherapy trials in autism targeting social impairment have yielded uniformly negative results. Accordingly, there is need for materials and methods for treating these conditions. Some aspects of the instant disclosure provide materials and methods for the study, diagnoses, and treatment of idiopathic and Fragile X Syndrome (FXS) linked Autism Spectrum Disorder (ASD).

SUMMARY OF THE INVENTION

A first embodiment includes methods for treating a patient, comprising the steps of: contacting a first sample of plasma from a patient diagnosed with ASD or FXS with at least one reagent that selectively binds to BDNF, ERK 1, ERK 2, sAPP, and/or sAPPa, determining the level of at least one of BDNF, ERK 1, ERK 2, sAPP, and/or sAPPa in the sample of plasma; administering at least one compound to the patient; binding a second sample of plasma from the patient with the at least one reagent that selectively binds to at least one of BDNF, ERK 1, ERK 2, sAPP, and/or sAPPa; determining if there is a change in the levels of one or more of the flowing compounds: BDNF, ERK 1, ERK 2, sAPP, and/or sAPPa in the patient's plasma; and adjusting the amount of the compound administered to the patient in response to the change in at least one of BDNF, ERK 1, ERK 2, sAPP, and/or sAPPa levels determined in the patient's plasma samples.

A second embodiment includes methods according to the first embodiment, wherein the first reagent is an antibody that selectively binds to BDNF or ERK1/2. A third embodiment includes methods according to the first embodiment, wherein the second reagent is an antibody that selectively binds to sAPP. A fourth embodiment includes methods according to the first embodiment, wherein the reagent is an antibody that selectively binds to sAPPa.

A fifth embodiment includes a method according to the first embodiment, including the steps of: elevating the level of BDNF in response to the administering step; and lowering the levels of ERK 1, ERK 2, sAPP, and sAPPa in response to the administering step.

A sixth embodiment includes methods according to the first through the fifth embodiments, wherein the compound is acamprosate or a pharmaceutically acceptable salt of acamprosate. A seventh embodiment includes methods according to the sixth embodiment wherein acamprosate is administered to the patient at a dose in the range of about 500 mg/day to about 1,500 mg/day.

An eighth embodiment includes systems for monitoring a patient, comprising: at least one first antibody that selectively binds to BDNF; at least one second antibody that selectively binds to sAPP; at least one antibody that binds to ERK 1 and/or ERK 2; and at least one antibody that selectively binds to sAPPα.

A ninth embodiments includes systems according to the eighth embodiment, further including: at least one reagent selected from the group consisting of: a buffer, a chelator; a bacteriacide, a fungicide, and a blocking agent.

A tenth embodiment includes methods for screening for a compound useful in the treatment of idiopathic autism or FXS linked ASD; comprising the steps of: contacting a first sample of plasma from a patient diagnosed with ASD or FXS with at least one reagent that selectively binds to at least one of BDNF, ERK 1, ERK 2, sAPP, and/or sAPPα; determining the levels of at least one of BDNF, ERK 1, ERK 2, sAPP, and/or sAPPα in the sample of plasma; administering at least one compound to the patient; binding a second sample of plasma from the patient with the at least one reagent that selectively binds to at least one of BDNF, ERK 1, ERK 2, sAPP, and/or sAPPα; determining if there is a change in the level of at least one of BDNF, ERK 1, ERK 2, sAPP, and/or sAPPα in the patient's plasma; and selecting the compound if that compound causes a change in the level of at least one of BDNF, ERK 1, ERK 2, sAPP, and/or sAPPα in the patient's plasma.

An eleventh embodiment includes the methods according to the tenth embodiment, wherein the first reagent is an antibody that selectively binds to BDNF. The twelfth embodiment includes the method according to the tenth embodiment, wherein the second reagent is an antibody that selectively binds to sAPP. The thirteenth embodiment includes the method according to the tenth embodiment, wherein the reagent is an antibody that selectively binds to sAPPα.

A twelfth embodiment includes the methods according to the tenth embodiment, including the steps of: accessing if the change caused by the compound is an increase in the level of BDNF, a decrease in the levels of sAPP, a decrease in the level of ERK 1 and/or ERK 2, and sAPPα. The thirteenth embodiment includes the methods according to the tenth embodiment further including the step of: altering the amount of the compound administered to the patient.

A thirteenth embodiment includes the methods according to the tenth embodiment, including the steps of: accessing if the change caused by the compound is a decrease in ERK1/2 activity measured in samples from a patient.

The fourteenth embodiment includes the methods according to the tenth embodiment further including the step of: altering the amount of the compound administered to the patient A fifteenth embodiment includes methods of treating a patient, comprising the steps of: administering a therapeutically effective amount of acamprosate or a pharmaceutically acceptable salt thereof to a patient; monitoring the patient's peripheral blood for a change in at least one of the following: ERK 1 or ERK 2, BDNF, sAPP, and sAPPα, levels in the patient's peripheral blood; and adjusting the therapeutically effective amount of the acamprosate or the pharmaceutically acceptable salt thereof such that the level of ERK 1 or ERK 2, BDNF and sAPP, and sAPPα, in the patient's peripheral blood changes. A sixteenth embodiment includes methods according to the tenth embodiment including the step of altering the amount of compound.

A seventeenth embodiment includes methods of treating a patient, comprising the steps of: administering a therapeutically effective amount of acamprosate or a pharmaceutically acceptable salt thereof to a patient; monitoring the patient's peripheral blood for a change in ERK 1, ERK 2, BDNF, sAPP, and/or sAPPα, levels in the patient's peripheral blood; and adjusting the therapeutically effective amount of the acamprosate or the pharmaceutically acceptable salt thereof such that the level of ERK 1, ERK 2, BDNF, sAPP, and/or sAPPα, in the patient's peripheral blood changes.

An eighteenth embodiment includes the methods according to the sixteenth embodiment, wherein the monitoring step includes: contacting a sample of the patient's peripheral blood with an antibody that selectively binds to BDNF. A nineteenth embodiment includes the methods according to the sixteenth embodiment, wherein the monitoring step includes: incubating a sample of the patient's peripheral blood with an antibody that selectively binds to sAPP. A twentieth embodiment includes the methods according to the sixteenth embodiment, wherein the monitoring step includes: probing a sample of the patient's peripheral blood with an antibody that selectively binds to sAPPα.

Twenty-first embodiments includes the methods according to the sixteenth through the seventeenths embodiments, wherein the adjusting step includes the step of increasing the amount of acamprosate such that the level of BDNF in the patient's peripheral blood increases and the levels of sAPP, and ERK1/2 activity, and sAPPae levels in the patient's peripheral blood decreases. A twenty-third embodiment includes methods according to the twentieth embodiment, wherein acamprosate is administered to the patient at a dose in the range of about 500 mg/day to about 1,500 mg/day.

Some embodiments include methods of treating a patient, comprising the steps of: elevating the serum level of BDNF in a patient, wherein said patient has been diagnosed with FXS. In some embodiments, the elevating step includes dosing the patient with a therapeutically effective level of acamprosate or a pharmaceutically acceptable salt of acamprosate.

Some embodiments include methods of treating a patient, comprising the steps of: reducing the serum level of ERK1/2 in a patient, wherein said patient has been diagnosed with FXS. In some embodiments, the reducing step includes dosing the patient with a therapeutically effective level of acamprosate or a pharmaceutically acceptable salt of acamprosate.

Some embodiments include methods of treating a patient, comprising the steps of: contacting a sample of plasma with a reagent that selectively binds to BDNF, wherein said sample of plasma is collected from a patient; determining the level of BDNF in the sample of plasma; and administering at least one compound to said patient such that the compound elevates the level of BDNF in the patient's plasma, wherein said patient has been diagnosed with FXS. In some embodiments, reagent is an antibody that selectively or at least preferentially binds to BDNF. In some embodiments, the compound that elevates the level of BDNF in the patient's serum is acamprosate or a pharmaceutically acceptable salt of acamprosate.

Some embodiments include methods of monitoring a patient, comprising the steps of: contacting a sample of plasma from a patient with at least one reagent that selectively binds to BDNF. In some embodiments these methods further include the steps of: administering at least one therapeutically effective dose of a compound to the patient; and testing plasma from the patient after the administering step by contacting serum collected from the patient with a reagent that selectively binds to BDNF. Still other embodiments may include the step of adjusting the dose of the compound to alter the level of BDNF that is present in patient's plasma. In some of these embodiments wherein the reagent that binds to BDNF is an antibody that specifically or at least preferentially binds to BDNF. In some embodiment the compound that alters the level of BDNF is acamprosate or a pharmaceutically acceptable salt thereof.

Some embodiments include methods for diagnosing autism disorders comprising the step of measuring the levels of secreted total amyloid-β precursor protein (sAPP), as wells as sAPPα, which is the secreted amyloid-β precursor protein after the cleavage of total holo-APP by α-secretase enzyme, in peripheral bodily fluids including the blood. Total sAPP comprises at least three species including sAPPα. Elevated levels of sAPP measured in youths are indicative of autism disorders, values in the range of greater than about 19 ng/mL are diagnostic for an increase in behavioral symptoms such as those employed in the Clinical Global Impression Improvement (CGI-I) scale.

Some embodiment include methods of treating patients diagnosed with autism disorder comprising the steps of measuring the levels of total sAPP and/or sAPPα before, during, and if necessary after treatment with a therapeutic dose or dosing regimen of a compound thought to reduce the symptoms of autism spectrum disorder. In some embodiments the compound is acamprosate and the therapeutic dose used to treat youths is proportional to the body weight of the patient and maybe in the range of 600-1998 mg/day). During treatment doses may be started a lower levels and are gradually increased to the noted ranges. Levels of sAPP and/or sAPPα measured in the patient's peripheral blood trigger and increase or decrease in the level of the therapeutic compound administered to the patient.

Some embodiments include method of predicting treatment options for patient with idiopathic or FXS linked ASD, theses method include the steps of measuring the plasma levels of BDNF, sAPP, and sAPPα in specific patients and treating patient that have lower than normal BDNF and higher than normal levels of sAPP and/or sAPPα in with compounds such as acamprosate that elevate BDNF and lower sAPP levels in some patient diagnosed with ASD.

Some embodiments include an analysis of fractional change from baseline to endpoint, mean sAPP total levels reduced from 34.7 (ng/mL) at baseline to 19.3 at endpoint (p=0.02) and mean sAPPα levels reduced from 7.8 (ng/mL) at baseline to 4.2 at endpoint (p=0.03).

DESCRIPTION

Figure 1:
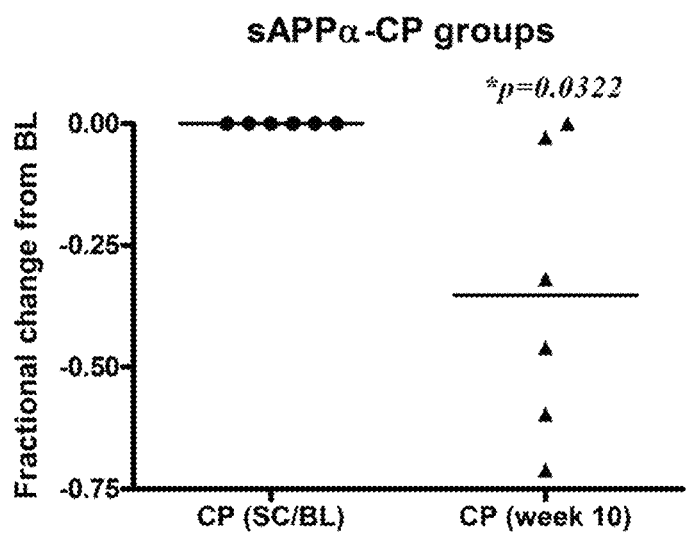
FIG. 1. Graph illustrating the relationship between the fractional change in sAPPα-CP levels measured in the blood of patients diagnosed with ASD and treated for 10 weeks with acamprosate.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Acamprosate has been approved by the FDA for treatment of alcohol dependence in adults. Acamprosate is a novel molecule potentially impacting both glutamate and gamma-aminobutyric acid (GABA) neurotransmission. Acamprosate is hypothesized to act as an antagonist at NMDA and metabotropic type 5 glutamate (mGluR5) receptors and as an agonist at GABA type A (GABA(A)) receptors. Excessive glutamatergic and deficient GABA(A) neurotransmission have been implicated in the pathophysiology of autistic disorder. The potential pharmacodynamic mechanisms of acamprosate are well matched to pathophysiology of autism. Additional information on the compound can be found in U.S. patent application Ser. No. 13/201,014 filed on Aug. 11, 2011, this patent application is incorporated herein by reference in its entirety.

Acamprosate is a unique drug which likely directly or indirectly impacts a number of neuro-receptors. Assessment of acamprosate's effect on biomarkers of potential significance in FXS holds promise to demonstrate the engagement of acamprosate with the pathophysiology of the disorder despite incomplete understanding of the proximal pharmacodynamic mechanisms of such action. Additionally, the social skills improvement noted in this report is consistent with findings described in our initial use of acamprosate in youth with idiopathic ASD (Erickson, et al. 2011). Given the overlap between FXS and ASD, it will be important in the future to assess the efficacy of acamprosate targeting the core social impairment associated with idiopathic ASD.

As used herein, unless explicitly stated otherwise or clearly implied otherwise, the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refers to a portion of a compound that has a net positive effect on the health and well being of a human or other animal. Therapeutic effects may include an improvement in longevity, quality of life and the like. These effects also may also include a reduced susceptibility to developing disease or deteriorating health or well being. The effects may be immediate realized after a single dose and/or treatment or they may be cumulative realized after a series of doses and/or treatments.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For addition information on some pharmaceutically acceptable salts that can be used to practice the invention please reviews such as Berge, et al., 66 J. PHARM. SCI. 1-19 (1977), Haynes, et al., J. Pharma. Sci., Vol. 94, No. 10, October 2005, pgs. 2111-2120 and the like.

Fragile X Syndrome (FXS) is the most common inherited form of developmental disability. The genetic mutation responsible for FXS is an unstable cysteine-guanine-guanine (CGG) trinucelotide repeat expansion (greater than 200 repeats) within the fragile X mental retardation 1 gene (fmr1). FXS is inherited via triplet expansion from a carrier (55-200 CGG repeats) parent, most commonly the mother. As an X-linked syndrome, FXS is more common in males, and the symptoms associated with the disorder are more marked in males. FXS is also a common single gene cause of autism spectrum disorders (ASD). It is estimated that 2 in 3 males with FXS have a co-occurring ASD diagnosis. There are very few treatments available for this devastating condition accordingly there is a need for additional therapies to treat this disease. Aspects of this invention seek to provide such therapies and tools for monitoring and implementing the same.

The triplet repeat expansion associated with FXS results in transcriptional silencing on the fmr1 gene resulting in absent fragile X mental retardation protein (FMRP). FMRP is a mRNA binding protein important to dendritic maturity and synaptic plasticity. In mouse brain, FMRP has been demonstrated to bind to hundreds of mRNA transcripts important to pre- and post-synaptic function.

In some animal studies, the lack of FMRP has been associated with dysregulated neurotransmission marked by excessive glutamatergic and deficient gamma-aminobutyric acid (GABA) signaling. Specifically, excessive metabotropic glutamate receptor 5 (mGluR5) activity is the best characterized element of dysregulated neurotransmission in FXS. In the fmr1 knockout mouse model, excess hippocampal and cerebellar long term depression (LTD), excess AMPA receptor internalization, abnormal dendritic morphology, and reduced seizure threshold are all consistent with excessive group 1, specifically mGLuR5, metabotropic glutamate receptor activation. The treatment implications of excessive mGluR activation in FXS have been thoroughly tested in FXS animal models and initially explored in human study. In the mouse model, mGluR5 down regulation by treatment with MPEP (2-methyl-6-(phenylethynyl)-pyridine) and other mGluR5 antagonists has been shown to reverse phenotypic characteristics, including audiogenic seizures, altered pre-pulse inhibition (PPI), and open field hyperactivity. Additionally, down regulation of mGluR5 executed by crossing a fmr1 knockout mouse with a mGluR5 heterozygous knockout resulted in reversal of several fmr1 knockout characteristics, including dendritic spine changes and excess protein synthesis.

Two human studies have reported on the use of selective mGluR5 antagonists in FXS. In a single dose pilot study involving 12 adults with FXS (6 males, 6 females; mean age=23.9 years), the mGluR5 antagonist fenobam showed variable pharmacokinetics and good tolerability marked by 3 subjects (25%) experiencing mild sedation. Clinically, 9 subjects (75%) reportedly experienced clinical benefit from single dose fenobam including reductions in hyperactivity and anxiety.

Interestingly, the use of the selective mGluR5 antagonist AFQ056 was not associated with significant group treatment effect in a double-blind, placebo-controlled two period crossover study in 30 males with FXS aged 18 to 35 years. In a 7 subject subset marked by full fmr1 gene methylation, significant response to AFQ056 compared to placebo was noted on several measures including the Aberrant Behavior Checklist (ABC) Stereotypy, Hyperactivity, and Inappropriate Speech subscales and total ABC score, Clinical Global Impressions Improvement (CGI-I) scale, the Visual Analogue Scale, and the Repetitive Behavior Scale-Revised. The authors hypothesized that AFQ056 may hold promise for treatment of interfering behaviors associated with FXS in a subgroup of persons with full fmr1 gene methylation. AFQ056 is currently the subject of large-scale Phase III clinical trials in FXS.

Aberrant ionotropic N-methyl-D-aspartic acid (NMDA) glutamate receptor signaling has been implicated in FXS. Upregulation of NMDA receptors at 2 weeks of life with the difference resolving by 6-7 weeks of age in fmr1 knockout mice has been reported. Use of the uncompetitive NMDA antagonist memantine was associated with correction of dendritic spine development and synapse formation in cultured cerebellar granule cells from fmr1 knockout mice. Modest effect of memantine use in 6 persons (mean age=18.3±3.8 years; range 13-22 years) with FXS and comorbid ASD were reported. In this study, four subjects (67%) showed clinical response as determined by a CGI-I score of "very much improved" or "much improved." Two subjects developed treatment limiting irritability during memantine treatment.

Deficiency of both GABA type A (GABA(A)) and GABA type B (GABA(B)) neurotransmission has been noted in FXS animal studies. FMRP has been shown to transcriptionally regulate GABA(A) receptor subunit RNA expression with reductions in GABA(A) receptor mRNA noted in FXS KO mice lacking FMRP. GABA(A) receptor expression has been shown to be significantly down regulated in a number of brain regions in fmr1 KO mice. In animal models of FXS, GABA(A) agonism has shown significant promise as a pharmacotherapy target. The GABA(A) agonist alphaxalone was associated with reductions in anxiety and rescue of audiogenic seizures in fmr1 KO mice. Also in FXS KO mice, the GABA(A) agonist gaboxadol restored neuron excitability deficits in the amygdala, reduced hyperactivity, and reduced PPI deficits. Improvements in memory acquisition and retention have been noted in FXS KO mice receiving taurine, a GABA(A) agonist. We are unaware of any trials of selective GABA(A) agonists that have been published involving persons with FXS.

Use of the selective GABA(B) agonist STX209 (arbaclofen, R-baclofen; a single enantiomer of baclofen) has been studied in both humans with FXS and in fmr1 knockout mice. In knockout mice, STX209 was associated with correction of aberrant protein synthesis and dendritic spine abnormalities. STX209 has been the subject of the largest published double-blind, placebo-controlled trial in FXS. In a crossover study adding STX209 to stable dosing of concomitant psychotropic drugs in 63 subjects aged 6 to 40 years with FXS, STX209 use was not associated with improvement on the primary outcome measure, the ABC Irritability (ABC-I) subscale. Group-wide effects were also not noted on global measures, including the CGI-I and CGI Severity (CGI-S) scales, other traditional subscales of the ABC (Social Withdrawal, Stereotypy, Hyperactivity, Inappropriate Speech), or the Visual Analog Scale (VAS). Overall, STX209 was well tolerated with only 8% of subjects reporting sedation. In post-hoc analysis, significant group-wide improvement with use of STX209 was noted on the Social Avoidance scale (ABC-SA), a newly developed 4-item subscale of the ABC specifically developed for potential use in persons with FXS. Also in post-hoc analysis, a 27 subject subset of persons with FXS and a baseline score of >8 on the ABC Social Withdrawal (ABC-SW) subscale significant STX209-associated improvement on the ABC-SW and the Vineland Adaptive Behavior Scales (VABS) Socialization measure of adaptive function. This study concluded that the drug holds promise targeting social deficits in persons with FXS. A large-scale Phase III study of STX209 in FXS is ongoing.

Acamprosate, (3-Acetamidopropane-1-sulfonic acid, also known as N-acetyl homotaurine) is a drug approved by the United States Food and Drug Administration (FDA) for the maintenance of abstinence from alcohol. It is prescribed for use in adults with alcohol dependence. FDA approved dosing in adults is 666 mg three times daily (two pills three times daily). In humans with alcohol dependence: lowers levels of several hormones: leptin, beta endorphin, cortisol.

The scientific literature includes reports that this molecule may be a potential antagonist a mGluR receptors. That it may act as an agonist at GABA(A) receptors in animal models Anti-oxidant effect in chronically alcohol ingesting rats. In rats this drug, elevates extracellular dopamine levels in the nucleus accumbens (dependent on glycine receptor activation). Acamprosate's potential effects include spermidine-sensitive NMDA receptors, enhanced activation at low glutamate concentrations and inhibition at high glutamate concentrations.

Some hypothesize that acamprosate blocks neurotoxic effects of mGluR agonist trans-ACPD. Reportedly, both 3-((2-Methyl-4-thiazolyl)ethynyl)pyridine (MTEP and acamprosate both reduced alcohol intake in the drinking-in-the-dark mouse model. MTEP and acamprosate both reported to reduce alcohol withdrawal associated anxiety effects in animals. Similar effects of 3-((2-Methyl-4-thiazolyl)ethynyl)pyridine (MTEP with increased sedative effects of alcohol withdrawal in mice have also been reported. It has also been reported that acamprosate and MPEP blocked in mGluR5 in knockout mice.

Acamprosate, an FDA approved drug used for the maintenance of abstinence from alcohol use in adults, is a bioactive agent with potential pleiotropic effects impacting at least glutamate and GABA neurotransmission. In animal studies, acamprosate has been demonstrated to bind and act as an antagonist at the NMDA glutamate receptor. A potential mGluR5 antagonist effect of acamprosate has been demonstrated in both animal models of alcoholism and depression. Additionally, acamprosate exhibits GABA(A) agonism in animal studies. Still, the exact mechanism of action of acamprosate in humans remain unknown particularly given findings in a *Xenopus* oocyte model noting no direct binding between acamprosate and glutamate or GABA receptors subtypes at clinically relevant concentrations.

A study with acamprosate and the pathophysiology of FXS, reported an initial clinical experience (Erickson, Mullett et al. 2010). In this study, 3 adult males (mean age=20.9 years) diagnosed with FXS were treated with acamprosate (mean dose=1,221 mg/day; mean duration=21.3 weeks). In this study, all 3 subjects showed significant positive clinical response as measured by the CGI-I with improvement noted primarily in social impairment and communication deficits. Two subjects experienced non-treatment limiting gastrointestinal distress (emesis and/or nausea). A first systematic prospective trial of acamprosate in youth with FXS was then conducted.

Blood biomarker development in FXS research holds potential promise to predict treatment response, define pharmacodynamic drug mechanisms including potential engagement of drug mechanism with underlying pathophysiologic features, and serve potentially as quantitative outcome measures. The value of these benefits are ever increasing given recent FXS clinical trial reports noting positive response in subgroups of subjects and the inherent subjective nature of relying on parent reported behavioral inventories or clinician rated outcome measures in FXS clinical research. Such markers once linked to efficacious treatment regimes are especially use in populations that are otherwise difficult to monitor and evaluate.

Brain derived neurotrophic factor (BDNF) is a protein that supports the survival of existing neurons and growth and differentiation of new neurons and synapses. In animal studies, BDNF has been shown to regulate expression of FMRP. Application of BDNF to hippocampal slices from fmr1 knockout mice has been demonstrated to rescue long-term potentiation (LTP) defects. BDNF expression has been shown to be reduced in fmr1 knockout mice compared to wild type littermates. Peripheral levels of BDNF have not been reported in humans with FXS and the impact of acamprosate use on BDNF levels is unknown.

As reported herein, each area of improvement, social behavior or inattention/hyperactivity, was captured utilizing multiple independent outcome measures thus strengthening each result. During the trial, families frequently commented on improvement in communication skills, a finding potentially supported by improvement noted during exploratory use of the VABS pre- and post-treatment. It remains unclear if acamprosate affected multiple areas of impairment independently or if improvement in one area, for example inattention/hyperactivity, led to associated improvement in other areas such as social behavior and communication. Aside from clearly measured improvements in the patients' behaviors and the newly identified biomarker for improvement the mechanistic results of the study were complicated by allowing some patient in the study the concomitant use of psychoactive drugs. Accordingly, it is possible that in some patients drug-drug interactions between acamprosate and concomitantly administered drugs may have impacted their treatment response and/or tolerability in ways that are not readily apparent given the relatively small number of patients enrolled in the study.

Regarding tolerability, limited gastrointestinal distress despite subjects at times chewing the enteric coated acamprosate tablets was noted. The low rate of gastrointestinal adverse effects was surprising given that adverse GI effects are the most common adverse effects noted with acamprosate use in alcoholism human study and in our first report on acamprosate use in FXS. Given the novelty of this trial, we did not have any historical data on which to base dosing other than data from the alcoholism literature where the drug has been dosed down to age 16 years (Niederhofer and Staffen 2003). Mild irritability noted in 4 subjects appeared to be dose-dependent on dose reduction in each case led to quick resolution of this adverse effect. It may be that in youth, once a threshold drug exposure is exceeded, mild irritability may occur in some participants with FXS. Overall, the final mean dose was about half of the dose that is FDA approved for use treating alcohol dependence in adults.

The BDNF findings showed consistent increases with use of acamprosate. This overall change in BDNF finding is potentially important in FXS given reports in fmr1 knockout mice of rescue of LTP deficits with BDNF application in hippocampus brain slices. This BDNF finding also may potentially provide some additional explanation for recent antidepressant qualities of acamprosate noted in an animal study (Louhivuori, Vicario et al. 2011) given cellular and behavioral models linking peripheral BDNF to the production of antidepressant-like effects (Uutela, Lindholm et al. 2012). BDNF may hold potential as both a possible predictor and measure of treatment response.

The lack of correlation between change in BDNF and treatment response noted with post-hoc analysis may be due to the small sample size and the fact that only one treatment non-responder had available pre- and post-treatment BDNF data. Use of concomitant medications renders BDNF interpretation more difficult. It is known that concomitant selective serotonin reuptake inhibitors (SSRIs) used in this trial likely increased BDNF (Balu, Hoshaw et al. 2008). Concomitant drug use dosing was kept stable throughout this trial to try and lessen variability introduced by concomitant drugs.

Mitogen-activated protein kinases (MAPKs) are important cell signaling molecules involved in several biological pathways. MAPKs are subdivided into several groups comprising extracellular signal regulated kinase (ERK), c-Jun amino-terminal kinase (JNK) and p38 isoforms. ERK1 and ERK2 are well-studied regulatory kinases and involved in wide varieties of cell signaling pathways. ERK 1/2 are phosphorylated on $Tyr^{204}$ and $Thr^{202}$ residues, translocate to nucleus and activate transcription of several genes. It was previously observed that subcellular localization of activated ERK 1/2 varies in different cells (or cell lines) and culture conditions. In the cultured mononuclear cells (isolated from patients), we have observed cytoplasmic localization of ERK 1/2 following Tamoxifen treatments (positive control). For individual patients and controls, we have counted the positive cells i.e. phospho-ERK 1/2 localized in the cytosolic compartment versus the total number of cells in the field. Ebisuya, M., Kondoh, K. and Nishida, E. (2005) *The duration, magnitude and compartmentalization of ERK MAP kinase activity: mechanisms for providing signaling specificity. Journal of cell science,* 118, 2997-3002.

The ERK1/2 subfamily of mitogen-activated protein (MAP) kinase mediates transmission of signals from cell surface receptors to cytoplasmic and nuclear effectors. In brain, ERK1/2 is most expressed in neurons compared to other cell types. Some results link potential ERK1/2 dysregulation to the pathophysiology of ASD. Conditional isoform 2 (ERK1/2) knockout mice have been shown to exhibit several features of relevance to ASD including reduced social behavior, defects in nest-building, and memory defects. In human genetic studies, deletion at chromosome 16p11.2, and deletion at chromosome 22q11.2, were the gene for ERK2 is located, have both been associated with autism. ERK1/2 signaling activity has been shown to be up-regulated in the BTBR mouse model of autism in human ASD post mortem study.

The Effect of Acamprosate on the Levels of BDNF in Patients Diagnosed with FXS Participants The Institutional Review Board (IRB) at an academic medical center approved this study. Thirteen outpatient males and females aged 5 to 17 years with body weight≥15 kg were recruited for this study. Written informed consent was obtained from each participant's legal guardian (parent for all children in this report), and subjects provided assent when able. Diagnosis of FXS was confirmed by Southern Blot and PCR results consistent with a greater than 200 CGG repeat expansion in the fmr1 gene with at least partial gene methylation. Subjects had to be free of other significant medical conditions. The concomitant use of psychotropic drugs that are not thought to impact glutamate neurotransmission were allowed so long as the patients experienced stable dosing at least 4 weeks prior to baseline. Subjects were required to have a mental age of greater than 18 months as determined by the Stanford-Binet 5th Edition. Additional inclusion criteria included a CGI-S (Guy 1976) score of at least 4 ("Moderately Ill"). Subjects with a Diagnostic and Statistical Manual of Mental Disorders, 4th Edition, Text Revision (DSM-IV-TR) diagnosis of a psychotic disorder, bipolar disorder, or substance use disorder were excluded from the study. Additionally, subjects with a positive urine pregnancy test, creatinine clearance of <30, active seizure disorder, or other significant medical condition were excluded.

Study Design

A 10-week, prospective, open-label study design was chosen to gather pilot data for potential future larger-scale, double-blind, placebo-controlled studies in this population.

Procedure

All subjects underwent a screening and baseline visit followed by follow-up visits every 2 weeks during the 10-week open-label trial period. At the end of weeks 1, 3, and 5 the investigators called the parent to assess drug tolerability and to make dose adjustments as indicated. All subjects received 333 mg/day of acamprosate during the first week of the study. The investigators then increased the dosage to a maximum of 1,998 mg/day (weight>50 kg) or 1,332 mg/day (weight<50 kg) over the first six weeks of the study, if optimal clinical response (CGI-I equal to 1 "very much improved") had not occurred and intolerable adverse effects had not emerged. The dose maintenance phase lasted 4 weeks at the optimal dosage.

Assessments

The CGI-S assessment was administered at screen and at baseline as part of the eligibility criteria described above. In this study, the rater scored the CGI-S in regard to severity of symptoms commonly noted in FXS including, but not limited to, inattention/hyperactivity, social impairment, communication impairment, repetitive behavior, irritability, and anxiety. The CGI-S is rated on a scale from 1 to 7 (1=normal, not ill at all; 2=borderline ill; 3=mildly ill; 4=moderately ill; 5=markedly ill; 6=severely ill; 7=among the most extremely ill patients with FXS). The Autism Diagnostic Observation Schedule (ADOS) (Lord, Rutter et al. 1989) was administered at baseline to characterize potential concomitant ASD diagnosis.

The primary outcome measure was the CGI-I. The CGI-I is a scale designed to assess global change from baseline. The CGI-I scores range from 1 to 7 (1=very much improved; 2=much improved; 3=minimally improved; 4=no change; 5=minimally worse; 6=much worse; 7=very much worse). Treatment response was defined by a CGI-I score of 1 "very much improved" or 2 "much improved." In this study, the CGI-I was utilized as a general global primary outcome measure given the uncertainty as to what specific symptoms/behaviors associated with FXS may be expected to improve or worsen with use of acamprosate. The CGI-I was administered at all visits after baseline.

Secondary outcome measures included all subscales of the ABC (Irritability, Social Withdrawal, Stereotypy, Hyperactivity, and Inappropriate Speech). The ABC is an informant-rated (primary caregiver) measure with confirmed reliability and validity with regard to factor structure, distribution of scores, and sensitivity to change in persons with developmental disability (Aman, Singh et al. 1985). Additionally, the ABC has shown good reliability and reproducibility in FXS-specific clinical research. Additional secondary outcome measures included the Social Responsiveness Scale (SRS) (Constantino, Davis et al. 2003), Compulsion Subscale of the Children's Yale-Brown Obsessive Compulsive Scale Modified for Pervasive Developmental Disorders (PDDs) (CY—BOCS-PDD) (Scahill, McDougle et al. 2006), CGI-S, and the ADHD Rating Scale 4th Edition (ADHD-RS) (Zhang, Faries et al. 2005). The SRS is a 65-item, parent-completed scale that assesses several aspects of reciprocal social behavior. The SRS gives a total score that is proportional to the level of impairment in reciprocal social behavior. The CY—BOCS-PDD uses the 5 compulsion severity items from the CY-BOCS using slightly modified anchor points that are more fitting for persons with ASD. The ADHD-RS is a standard clinician scored rating scale widely utilized in ADHD drug trials. All secondary outcome measures were administered at all study visits.

Additional exploratory outcome measures administered at baseline and Week 10 included the Vineland Adaptive Behavior Scales (VABS) (Sparrow and Cicchetti 1985), and Clinical Evaluation of Language Fundamentals, 4$^{th}$ Edition (CELF) (Muma 1984). The VABS was utilized to detect potential change in adaptive behavior with treatment. The PPVT and CELF were included to capture potential change in communication/language.

Safety assessment and monitoring began at screen when all subjects underwent a medical history, physical examination, and full psychiatric interview. A physical examination was also completed at end point. Vital signs, including height and weight, were obtained at each study visit. At screen, genetic testing for FXS was obtained if record of molecular testing utilizing Southern Blot and PCR was not available. At screen, week 6, and endpoint, laboratory tests of blood and urine, including CBC with differential and platelets, electrolyte panel, liver associated enzymes, lipid panel, and urine pregnancy test (in females) were obtained. An electrocardiogram was also obtained at screen and endpoint.

Biomarker Assessment

Blood samples for BDNF were drawn at Screen and at Week 10 of the study. BDNF analysis was done blind to patient assignment (pre- or post-treatment). Approximately 4 ml of blood was collected in EDTA containing tubes. Within 30 minutes of collection, the blood was centrifuged at 1000 g at 2-8° C. for 15 minutes. Plasma was collected and an additional centrifugation of the collected plasma at 1000 g at 2-8° C. for 10 minutes was done to completely remove platelets from the samples. All plasma samples were stored at −80° C. BDNF assays were done at the same time with all samples in triplicate. To determine plasma BDNF, a sensitive ELISA based method was used using human BDNF ELISA kit from R&D systems (Minneapolis, Minn.; USA) that is validated for detection of BDNF present in human plasma (Grassi-Oliveira et al., 2008). The amount (µg/ml) of BDNF present in the plasma samples was determined from the pg value obtained in the standard curve using a known amount of pure human BDNF, which was run at the same time with subjects' samples.

Data Analysis

All data were recorded in SPSS Statistics Professional for statistical analysis. Potential differences in pre- and post-treatment mean values of all outcome measures employed were calculated using paired t-tests. In cases where data failed the normality assumption, Wilcoxan signed-rank tests were utilized to assess potential change in pre- and post-treatment mean values. Effect sizes were calculated by taking the mean change from baseline to endpoint divided by the standard deviation at baseline.

Of 13 subjects screened, 12 (92%) met eligibility criteria and were enrolled. The recruited sample consisted of 10 males and 2 females (age range, 6-17 years; mean 11.9 years). Ten subjects (83%) met ADOS criteria for an additional diagnosis of autistic disorder and two (17%) met criteria for pervasive developmental disorder not otherwise specified (PDD-NOS). Full scale intelligence quotient ranged from 36-61, with a mean score of 45. Subjects received a mean final dose of acamprosate of 1054 mg/day (range, 666-1,998 mg/day). Ten subjects used concomitant psychotropic drugs during the study (mean 2.3 concomitant psychotropic drugs), including most commonly atypical antipsychotics (n=7; Table 1) and stimulants (n=4).

TABLE 1

Concomitant Psychotropic Drug Use in Participants in BDNF Study

| Drug | Number of Subjects |
| --- | --- |
| Risperidone | 4 |
| Aripiprazole | 2 |
| Fluoxetine | 2 |
| Methylphenidate ER | 2 |
| Mirtazapine | 2 |
| Sertraline | 2 |
| Clonidine | 2 |
| Dexedrine | 1 |
| Guanfacine | 1 |
| Lisdexamphetamine | 1 |
| Lorazepam | 1 |
| Oxcarbazepine | 1 |

All subjects completed the entire study. Nine (75%) of twelve subjects were considered treatment responders based on a CGI-I score of 1 "very much improved" (n=5) or 2 "much improved" (n=4). The mean CGI-I at endpoint was 1.9.

Among additional outcome measures, significant improvements were noted in social behavior and inattention/hyperactivity. Regarding social behavior, mean scores on the ABC-SW subscale declined 53% from 8.8 at baseline to 4.1 at endpoint (p=0.04; effect size=0.81). Mean scores on the ABC-SA declined 51% from 3.3 at baseline to 1.6 at endpoint (p=0.01; effect size=0.64).

In addition to ABC findings consistent with change in social behavior, the SRS changes noted with treatment were consistent with reductions in social impairment. Mean total SRS raw scores declined 16% from 91.3 at baseline to 76.4 at endpoint (p=0.005; effect size 0.54). Among treatment subscales of the SRS, improvement was noted in Social Cognition (19% decline; p=0.01), Social Communication (14% decline; p=0.01), and Social Motivation (28% decline; p=0.003). Improvement was not noted on the SRS Social Awareness and Autistic Mannerisms subscales.

Improvement in hyperactivity was noted on the ABC Hyperactivity subscale (ABC-H) where mean scores declined 35% from 16.8 at baseline to 11.0 at endpoint (p=0.01; effect size=0.64). Consistent with the ABC-H subscale finding, mean scores on the ADHD-RS declined 29% from 23.6 at baseline to 16.7 at endpoint (p=<0.0001; effect size=0.65).

Global severity of illness improved as exhibited by a mean CGI-S change from 4.25 (between moderately and severely ill) to 3.33 (between mildly and moderately ill) at endpoint (p=<0.0001; effect size=2.0). Other subscales of the ABC and the CY—BOCS-PDD did not change significantly during treatment (Table 2).

Among exploratory outcomes measures, PPVT scores did not significantly change with treatment. The CELF proved difficult to administer with only 3 subjects obtaining valid pre- and post-treatment scores. Among domains of the VABS, mean Communication Domain standard scores improved 5% from 63.4 at baseline to 66.6 at endpoint (p=0.03; effect size=0.3). Within VABS sub-domains, Expressive Communication mean scores improved 13% from 69.7 at baseline to 78.9 at endpoint (p=0.003; effect size=0.4). No other changes with treatment were noted on the VABS.

TABLE 2

Outcome Measures in Subject Treated with Acamprosate

| Measure | Baseline (mean ± SD) | End point (mean ± SD) | P value | Effect Size[a] | T value | Degrees of Freedom |
|---|---|---|---|---|---|---|
| Aberrant Behavior Checklist-Irritability (ABC-I) | 9.9 ± 7.8 | 7.0 ± 8.9 | 0.11 | — | 1.76 | 11 |
| Aberrant Behavior Checklist-Social Withdrawal (ABC-SW) | 8.8 ± 5.8 | 4.1 ± 6.5 | 0.04 | 0.81 | 2.35 | 11 |
| Aberrant Behavior Checklist-Stereotypy (ABC-S) | 6.8 ± 6.8 | 6.0 ± 6.3 | 0.09 | — | 1.89 | 11 |
| Aberrant Behavior Checklist-Hyperactivity (ABC-H) | 16.8 ± 9.1 | 11.0 ± 8.6 | 0.009 | 0.64 | 3.19 | 11 |
| Aberrant Behavior Checklist-Inappropriate Speech (ABC-IS) | 5.2 ± 3.5 | 4.8 ± 3.4 | 0.61 | — | 0.53 | 11 |
| Aberrant Behavior Checklist-Social Avoidance (ABC-SA) | 3.3 ± 2.6 | 1.6 ± 2.7 | 0.01 | 0.64 | 2.93 | 11 |
| Clinical Global Impressions-Severity (CGI-S) | 4.25 ± 0.45 | 3.33 ± 0.5 | <0.0001 | 2.0 | 6.17 | 11 |
| Children's Yale-Brown Obsessive Compulsive Scale Modified for PDD (CY-BOCS-PDD) | 11.1 ± 2.6 | 9.8 ± 4.1 | 0.15 | — | 1.53 | 11 |
| Social Responsiveness Scale total score (SRS) | 91.3 ± 27.4 | 76.4 ± 26.8 | 0.005 | 0.54 | 3.52 | 11 |
| ADHD Rating Scale 4th Edition (ADHD-RS) | 23.6 ± 10.6 | 16.7 ± 8.0 | <0.0001 | 0.65 | 5.14 | 11 |
| Peabody Picture Vocabulary Test (PPVT) | 85.2 ± 32.0 | 83.3 ± 32.0 | 0.53 | — | 0.65 | 10 |
| Vineland Adaptive Behavior Scale (VABS) Communication Domain | 63.4 ± 10.1 | 66.6 ± 11.2 | 0.03 | 0.32 | −2.45 | 11 |
| VABS Expressive Communication Subdomain | 69.8 ± 23.0 | 78.9 ± 21.2 | 0.003 | 0.4 | −3.72 | 11 |

[a]Effect Size only computed for corrected p values ≤ 0.05; Computed as mean change from baseline to endpoint divided by SD at baseline.
SD = Standard Deviation.

Ten subjects (83%) participated in screen and Week 10 plasma BDNF sampling. Two subjects failed to have sufficient blood at Week 10 drawn for biomarker sampling (priority was given to safe laboratory measures). All BDNF data was analyzed used Wilcoxan signed-rank tests. All subjects experienced an increase in plasma BDNF from screen to Week 10. Mean subject plasma BDNF increased with treatment from 790.4±1350.4 pg/mL to 1007.6±1493.2 pg/mL (p=0.01). Post-hoc analysis of potential correlation of BDNF change and Wekk 10 CGI-I score were carried out. In our 10 subjects with available BDNF data, 9 of which were treatment responders, there was no correlation between change in BDNF level and treatment response (P=0.2; sign test).

Safety Measures and Adverse Effects

No clinically significant changes in weight, pulse, or blood pressure were noted. No clinically significant changes were noted on ECG, including no change in the QTc interval. Regarding laboratory measures, no clinically significant or mean changes were noted in lipids, electrolytes, liver function tests, or blood counts.

Acamprosate was well tolerated overall, with no severe or serious adverse effects recorded during the study. Nine subjects (75%) experienced a mild adverse event during the study. The most common mild adverse effects as reported by caregivers included irritability (n=4) and increased repetitive behavior (n=2). All cases of irritability appeared dose-dependent with irritability abating in each case with a 333 mg dose reduction. No cases of mild irritability remained by the Week 10 visit. Gastrointestinal adverse effects included mild diarrhea (n=1) and mild constipation (n=1).

TABLE 3

Caregiver Reported Adverse Effects of Acamprosate Treatment.

| Adverse Event | Mild (n) |
| --- | --- |
| Irritability | 4 |
| Increased Repetitive Behavior | 2 |
| Constipation | 1 |
| Diarrhea | 1 |
| Increased Anxiety | 1 |
| Insomnia | 1 |
| Nightmares | 1 |
| Rhinitis | 1 |
| Urinary Urgency | 1 |

Effect of Acamprosate on sAPP, sAPP a Levels in Patients Diagnosed with Autistic Spectrum Disorder Overview Amyloid-beta precursor protein (APP) is a protein likely important for synapse formation. The amyloidogenic pathway of APP cleavage leads to the production of amyloid beta peptide (Aβ), the main component of plaques associated with Alzheimer disease. The non-amyloidogenic pathway yields the neurotrophic product secreted APPα (sAPPα). In youth with autism, potential increased activity of the non-amyloidogenic pathway marked by increased serum total sAPP and sAPPα has been noted. It does appear as though sAPP has been studied as a potential marker and predictor of treatment response in clinical trials involving persons with autistic spectrum disorder.

Acamprosate is a novel molecule potentially impacting both glutamate and gamma-aminobutyric acid (GABA) neurotransmission1. APP is important to synapse formation. The amyloidogenic pathway of APP cleavage leads to the production of amyloid beta peptide (Aβ), the main component of plaques associated with Alzheimer's disease. The non-amyloidogenic pathway yields the neurotrophic product secreted APPα (sAPPα). Total plasma APP (sAPP total) and plasma sAPPα have been found in multiple studies to be elevated in youth with ASD compared to neurotypical control subjects2,3. These findings, combined with evidence of brain overgrowth contributing to the pathophysiology of idiopathic ASD, has led to the hypothesis that excessive sAPPα activity may play a role in the pathogenesis of ASD2. Specifically in FXS, fragile X mental retardation protein (FMRP) is known to regulate APP translation with resultant APP elevation noted in FXS given absent FMRP4. Overall, there is evidence in idiopathic and FXS-associated ASD warranting exploration of APP, specifically sAPPα, modulation as a potential pharmacodynamic mechanism of importance.

In an initial clinical experience with acamprosate treatment in youths symptomatic for an autistic disorder five of six youths (mean age=9.5 years) treated with acamprosate were judged treatment responders to acamprosate (mean dose=1,110 mg/day) over 10 to 30 weeks (mean duration=20 weeks) of treatment. Amyloid-beta precursor protein (APP) is a protein likely important for synapse formation. The amyloidogenic pathway of APP cleavage leads to the production of amyloid beta peptide (AB), the main component of plaques associated with Alzheimer disease. The non-amyloidogenic pathway yields the neurotrophic product secreted APPα (sAPPα). In youth with autism, potential increased activity of the non-amyloidogenic pathway marked by increased serum total sAPP and sAPPα has been noted. It appears as though sAPP is a potential marker and predictor of treatment response in clinical trials involving persons with autistic spectrum disorder. As disclosed herein, sAPP found in the blood has been found to be an unexpectedly accurate bio-marker for autism spectrum disorder.

Assays for sAPP and sAPPα

Test plasma samples are measured soon after collection. When necessary test samples of plasma were frozen but not subjected to repeated freeze/thaw cycles. The test samples were thawed just before use at a low temperature and mixed them completely. If necessary, the plasma samples can be diluted appropriately with the EIA buffer, and assay may be performed in duplicate measurements for the test samples and standards. Test samples in neutral pH range were used, and steps were taken to avoid the contamination with of organic solvents. Regarding the standard to quantify the sAPPα levels, a series of sAPPα standards in EIA buffer by serial dilutions, from 0.78 ng/mL to 50 ng/mL were prepared.

The ELISA plates were pre-coated with anti-human sAPPα (2B3) mouse IgG-monoclonal affinity purified (IBL). First, the wells for the reagent blank were determined, and 100 µL each of "EIA buffer" or 10 mM NaHCO₃ (pH9.5) buffer was placed into each of the wells. Likewise, wells were assigned for test sample blanks, test samples and diluted standards. Next, 100 µL each of test sample blank, test sample and dilutions of standard was added to into the appropriate wells. The test sample included the plasma sample from each subject, which may vary from 5-25 µl, made up to 100 µL with the EIA buffer. The pre-coated plate was incubated overnight at 4° C. after covering it tightly with a plate lid. The plate was kept onto a rocker with gentle shaking. Next day, each well of the pre-coated plate was vigorously washed with wash buffer containing 0.05% Tween 20 in phosphate buffer. This was done by filling each well with the wash buffer, leaving the pre-coated plate laid for 15-30 seconds and removing wash buffer completely from the plate by snapping. This procedure was repeated five times. After removing the remaining liquid from all wells completely by snapping the plate onto paper towel, 100 μL of labeled antibody solution was added into the wells of test samples, diluted standard and test sample blank. HRP-conjugated and labeled anti-Human APP (R101A4) mouse IgG from IBL was used. Each plate was incubated for 30 minutes at 4° C. after covering it with plate lid, and then washed the plate 5 times in the same manner as described before. To develop the color, 100 μL of the Chromogen (TMB solution) was added to into the wells, and the plate was incubated for 30 minutes at room temperature in the dark. When the liquid started turning blue (by addition of the Chromogen), 100 μL of the Stop solution (1N $H_2SO_4$) was added into the wells. The liquid was mixed by tapping the side of plate, and the liquid turned yellow by addition of the Stop solution. Care was taken to exclude any dirt or drops of water on the bottom of the plate and it was ensured there was no bubble on the surface of the liquid. A plate reader was used and measurements were conducted measurement at 450 nm against a reagent blank. The measurement was generally done within 30 minutes after addition of the Stop solution. Chromogen is stored in the dark due and kept free of metals.

ELISA of sAPP:

For sAPP levels, the Test plasma samples should be measured soon after collection. For the storage of test samples, we stored the plasma samples them frozen and did not repeat freeze/thaw cycles. Just before assay, we thawed the test samples at a low temperature and mixed them completely. The plasma samples should be diluted appropriately with the EIA buffer, if needed. Duplicate measurement of test samples and standard are recommended. We used test samples in neutral pH range, and avoided the contaminations of organic solvent that may affect the measurement. Regarding the standard to quantify levels of sAPP, we prepared a series of sAPP standards in EIA buffer by serial dilutions, from 0.39 ng/mL to 25 ng/mL.

The ELISA plate was pre-coated with anti-human APP (R12A1) mouse IgG (IBL). First, the wells for reagent blank was determined, and 100 μL each of "EIA buffer" or 10 mM $NaHCO_3$ buffer was added into the wells. Likewise, wells were assigned for test sample blank, test sample and diluted standard. Then 100 μL each of test sample blank, test sample and dilutions of standard was added into the appropriate wells. The test sample included the plasma sample from each subject, which may vary from 5-25 μl, made up to 100 μL with the EIA buffer. Each pre-coated plates was incubated overnight at 4° C. after covering it tightly with a plate lid. The plate was kept onto a rocker with gentle shaking. The next day, each well of the pre-coated plate was vigorously washed with wash buffer containing 0.05% Tween20 in phosphate buffer. This was performed by filling each well with wash buffer, leaving the pre-coated plate laid for 15-30 seconds and removing wash buffer completely from the plate by snapping. This procedure was repeated five times. After removing the remaining liquid from all wells completely by snapping the plate onto paper towel, we added 100 μL of labeled antibody solution into the wells of test samples, diluted standard and test sample blank. HRP labeled anti-Human APP (R101A4) mouse IgG from IBL was used. The plate was incubated for 30 minutes at 4° C. after covering it with plate lid, and then washed the plate 5 times in the same manner as described before. To develop the color, 100 μL of the Chromogen (TMB solution) was adding into the wells, and the plate was incubated for 30 minutes at room temperature in the dark.

When the liquid started turning blue (by addition of the Chromogen), 100 μL of the Stop solution (1N $H_2SO_4$) was added into the wells. The liquid was mixed by tapping the side of plate, and the liquid turned yellow by addition of the Stop solution. Any dirt or drop of water on the bottom of the plate was removed and all plates were checked to ensure that there were no bubbles on the surface of the liquid. A plate reader was used and measurements were conducted at 450 nm against a reagent blank. The measurement was generally done within 30 minutes after addition of the Stop solution.

Summary of Clinical Trials

Clinical trials of acamprosate in youth with ASD were carried out. One study enrolled 12 youth with idiopathic ASD. Still another study enrolled 12 youth with fragile X syndrome (FXS)-associated ASD. Pre- and post-acamprosate sAPP total and sAPPα levels were available from 15 participants (9 with FXS, 6 with idiopathic ASD). The subjects mean IQ was 56 (range 36 to 96). The subjects final acamprosate dosing was 1,054 mg/day. Overall, sAPP total reduced with use of acamprosate from a mean 32.6±38.3 ng/mL pre-treatment to 21.4±32.3 ng/mL post-treatment (p=0.01). sAPPα reduced with use of acamprosate from a mean 8.4±7.9 ng/mL pre-treatment to 5.5±7.2 ng/mL post-treatment (p=0.003). Reduction of peripheral sAPP total and sAPPα induced by treatment with acamprosate points towards a mechanism for targeting the pathophysiology of ASD.

One study was a 12-week single-blind, placebo-controlled trial of acamprosate in 12 youths with autistic disorder was conducted. The primary outcome measured was the Clinical Global Impression Improvement (CGI-I) scale with several additional behavioral secondary outcome measures employed. In this study, secreted amyloid precursor protein (sAPP) was measured pre- and post acamprosate treatment as blood biomarker assay Result: Twelve subjects (mean age=10.4 yrs.) entered the study and nine subjects completed a two week placebo lead-in and entered active treatment (mean final dose=1,073 mg/day). Six of nine (67%) subjects receiving acamprosate were judged treatment responders with a CGI-I score of 1 "very much improved" or 2 "much improved". Overall acamprosate use was well tolerated with no adverse effects leading to drug discontinuation or laboratory/vital sign abnormalities noted. Among secondary outcome measures analyzed, significant acamprosate-associated improvement was noted on measures of social behavior and hyperactivity. Acamprosate use was also associated with reductions in sAPP levels. These results demonstrate that Acamprosate can reduce social deficits associated with autism in some patients that that sAPP measured in the blood is a useful biomarker for diagnosing the disease and for monitoring the efficacy of pharmacological treatments for the disorder.

In total, twenty-four youth (mean age 11.1 years; range 5-17 years) participated in these two pilot clinical trials. Fifteen subjects had available pre- and post-acamprosate sAPP total and sAPPα assay data available. Post-treatment blood samples were not available from 3 subjects with FXS, 3 subjects with ASD were deemed placebo lead-in responders and did not receive acamprosate, and 3 subjects receiving acamprosate in the idiopathic ASD study were lost to follow-up during active acamprosate treatment and did not complete post-treatment blood analysis. Using pre-specified indicators of clinical response, 9 of 12 youth with FXS and 6 of 9 youth with idiopathic ASD were judged responders to acamprosate. Generally, clinical improvement was noted in social behavior and inattention/hyperactivity. Pooled subject mean IQ was 56 (range 36 to 96). Pooled subjects final acamprosate dosing was 1,054 mg/day. Overall, sAPP total reduced with use of acamprosate from a mean 32.6±38.3 ng/mL pre-treatment to 21.4±32.3 ng/mL post-treatment (p=0.01). sAPPα reduced with use of acamprosate from a mean 8.4±7.9 ng/mL pre-treatment to 5.5±7.2 ng/mL post-treatment (p=0.003). Levels of both sAPP total and sAPPα reduced with treatment in every sample tested except in one subject with idiopathic ASD where sAPPα was unchanged following treatment. No significant correlations between percent change in sAPP total or sAPPα and percent change in scores on the ABC-SW were noted in the pooled 15 subject sample. Within the 9 subject subset of those with FXS, a significant correlation was noted between change in sAPP total and ABC-SW scores meaning that more reduction in sAPP total correlated with greater improvement in ABC-SW scores (Spearman Correlation Coefficient=0.853; p=0.003).

The first project enrolled 12 youth aged 5 to 17 years with fragile X syndrome and comorbid ASD in a 10-week open-label trial of acamprosate. The second project enrolled 12 youth aged 5 to 17 years diagnosed with idiopathic ASD in a 12-week single-blind placebo lead-in study of acamprosate. In both projects, concomitant dosing of psychotropic drugs remained stable throughout study. In each project, pre- and post-acamprosate treatment plasma levels of sAPP total and sAPPα were obtained. All APP assay samples were collected, chilled, and walked within 2 hours of blood draw to the lab for analysis. Plasma sAPP total and sAPPα were determined separately in serum using the ELISA kit obtained from Immuno Biological Laboratories (IBL, Gumma, Japan). The ELISA kit is validated to measure levels of sAPPα in human samples and able to detect as low as 0.09 ng/ml of sAPPα in a typical sample, with only 0.3% cross-reactivity to sAPP. Levels of sAPP total and sAPPα in plasma were reported in nanograms per milliliter (ng/mL). Statistical analyses of pre- and post-acamprosate sAPP total and sAPPα levels were conducted using paired T-tests. Finally an exploratory post-hoc analysis of potential correlation between percent change in sAPP total or sAPPα and percent change in scores on the Aberrant Behavior Checklist Social Withdrawal/Lethargy subscale (ABC-SW) was conducted. The ABC-SW measures social impairment which is a core symptom domain of ASD. Post-hoc analysis was done with Spearman correlation calculations. All data was analyzed in IBM SPSS Version 20.

Twelve youth (mean age 10.4 years; range 5-15 years) participated in this study. Subjects' mean IQ was 67 (range 25-96). Nine subjects entered the active treatment phase (beyond week 2 visit). One subject was deemed a placebo responder, one subject developed significant irritability during placebo treatment and exited the study, and one subject experienced significant emesis and diarrhea on placebo and exited the study. Among nine patients who received acamprosate, the mean final drug dose was 1,073 mg/day (range 600-1,998 mg/day). Overall acamprosate was well tolerated with no adverse effects leading to drug discontinuation and no vital sign or safety laboratory changes noted. Adverse effects during acamprosate treatment included: mild transient diarrhea (n=3), dose related transient irritability that abated with dose reduction (n=2), mild transient headaches (n=2), mild transient tiredness (n=2), mild transient insomnia (n=2), mild transient excessive laughter (n=1), and mild transient increased hyperactivity (n=1). Regarding behavioral outcome measures, to date we have analyzed data from the CGI-I, CGI-S, all subscales of the ABC, the SRS, and the ADHD-RS. All analyses are made using last observation carried forward as three subjects were lost to follow up prior to week 12 (one each lost after weeks 6, 8, and 10 respectively). Six of nine subjects (67%) entering the active treatment phase were judged acamprosate responders with a CGI-I score of 1 or 2 (mean CGI-I at last visit=2).

Among secondary outcome measure data analyzed to date (paired t-tests), improvement with acamprosate use was noted on the SRS total raw score (mean change from 107+/−28 at baseline to 91.4+/−30 at endpoint; p=0.002), ABC Lethargy/Social Withdrawal subscale (ABC-SW; 14.1+/−8.5 to 10.0+/−8.4; p=0.019), the ADHD-RS (29.5+/−10.4 to 20.75+/−9.7; p=0.002), the ABC Hyperactivity subscale (25.4+/−12.6 to 16.6+/−12.4; p=0.005), and the CGI-S (4.22+/−0.4 to 3.7+/−0.5; p=0.013). Regarding sAPP blood biomarker data, by study conclusion six subjects has pre- and post-acamprosate sAPP total and sAPPα levels available. In analysis of fractional change from baseline to endpoint, mean sAPP total levels reduced from 34.7 (ng/mL) at baseline to 19.3 at endpoint (p=0.02) and mean sAPPα levels reduced from 7.8 (ng/mL) at baseline to 4.2 at endpoint (p=0.03).

This initial pilot placebo-controlled trial of acamprosate targeting social impairment in youth with autism, demonstrated that the drug to be well tolerated with potential signs of efficacy noted specific to reductions in social deficits and hyperactivity. This study demonstrates that acamprosate use was associated with significant and uniform reductions in sAPP total and sAPPα pointing to a potential pharmacodynamics marker of treatment effect in autism.

A 12-week single-blind, placebo-controlled trial of the effect of acamprosate in the treatment of 12 youths with autistic disorder aged 5 to 17 years was carried out. In order to pilot test use of acamprosate in youth with autism targeting core social impairment, was conducted. All subjects and their family members were blinded to treatment status. All subjects participated in a 2 week placebo-lead-in phase prior to 10 weeks of treatment with acamprosate. For this project, enteric coated commercially available 333 mg acamprosate pills were over-encapsulated and identical matching placebo manufactured for the project. Placebo-responders, defined by a Clinical Global Impressions Improvement scale (CGI-I) score of 1 "very much improved" or 2 "much improved" (ratings anchored to core social deficits) at week 2 were asked to exit the study. During active treatment with acamprosate, dosing was increased in 333 mg increments per week over the first six weeks of active treatment to a maximum dose of 1,332 mg/day (weight<5 60 kg) or 1,998 mg/day (weight>60 kg). During the final four weeks of active drug treatment, subjects were maintained on a stable highest tolerated (optimal) dose. The primary outcome measure was the clinician-rated CGI-I anchored to symptoms of social impairment. Secondary outcome measures included the CGI-Severity scale, the Aberrant Behavior Checklist (ABC), Children's Yale Brown Obsessive-Compulsive Scale Modified for Pervasive Developmental Disorders (CY-BOCS PDD), ADHD Rating Scale 4th Edition (ADHD-RS), Social Responsiveness Scale (SRS), Vineland Communication Subscale, Peabody Picture Vocabulary Test (PPVT), the Repeatable Battery for Assessment of Neuropsychological Status (RBANS), and expressive language sampling. Each subject completed IQ testing utilizing the Stanford Binet 5th Edition at screen. Additionally, sAPP samples were drawn at baseline and at study conclusion. Safety laboratory studies were drawn at screen, week 6 and week 12. A physical exam was done at screen and week 12 and vital signs were obtained at all study visits.

Potential acamprosate adverse effects were elicited at all study visits and interval study physician phone calls utilizing an adverse effect log.

Effect of Acamprosate on sAPP, sAPPα in Patients Diagnosed with FXS-linkedASD.

Twelve youths aged 5-17 were enrolled in an open label study. All 12 subjects were confirmed by Southern Blot and/or PCR Analysis to have full FXS mutations. The subjects were further screened for IQ (SB5 or Leiter) ADI-R, ADOS Vineland.

The pilot study ran for 10 weeks. Safety lab screens were carried out at weeks 6 and 10. Physiologic parameters measured during the safety screens were as follows: vital signs, LFTs, electrolyte panels, CBC with diff/plts, lipid panel, glucose, urinalysis and ECG.

In-person clinical visits were scheduled for every two weeks. Telephonic evaluations were carried out at weeks 1, 3, and 5. Each subject was evaluated for side effects at every interaction with the practitioner.

A flexible dosing regime was used. Enteric coated acamprosate tablets in 333 mg. amounts were used. Dosing was increased in 333 mg. increments weekly for the first 6 weeks of the study. For subjects with a body weight of less than 50 kg., maximum dose was 1332 mg. (divided BID or TID). For subjects with a body weight of greater than 50 kg., maximum dose was 1998 mg. (divided BID or TID). The mean final dose was 1054+/−422 mg. per day.

Thirteen subjects were screened for this study. One of the subjects could not swallow pills and was excluded from this study. The remaining subjects included 10 males and 2 females. Their mean age was 11.9 years, ranging from 6.25 to 17.75 years. The mean IQ of the 12 subjects was 44.6, ranging from 36 to 61. Ten of the subjects were diagnosed with autistic disorder and two were diagnosed with pervasive developmental disorder NOS.

By study's end 75% of the subjects (9/12) were deemed to be responders. These 9 subjects had CGI-I scores of 1 (very much improved) or 2 (much improved). The mean CGI-I values for the responders at week 10 was 1.92.

TABLE 4

Parameters measured in patients diagnosed with FXS-linked ASD and treated with acamprosate.

| Secondary Outcome Measures Reviewed | Secondary Outcome Measures to be Analyzed |
|---|---|
| Aberrant Behavior Checklist (ABC) | Children's Yale-Brown Obsessive Compulsive Scale Modified for PDDSs (CYBOCS PDD) |
| Social Responsiveness Scale (SRS) | Vineland Communication |
| Clinical Global Impressions-Severity Scale (CGI-S) | Clinical Evaluation of Language Fundamentals (CELF-4) |
| Peabody Picture Vocabulary Test (PPVT) | Expressive Language Sampling |

Among secondary outcomes measured data was analyzed to date (paired t-tests), improvement with acamprosate use was noted on the SRS total raw score (mean change from 107+/−28 at baseline to 91.4+/−30 at endpoint; p=0.002), ABC Lethargy/Social Withdrawal subscale (ABC-SW; 14.1+/−8.5 to 10.0+/−8.4; p=0.019), the ADHD-RS (29.5+/−10.4 to 20.75+/−9.7; p=0.002), the ABC Hyperactivity subscale (25.4+/−12.6 to 16.6+/−12.4; p=0.005), and the CGI-S (4.22+/−0.4 to 3.7+/−0.5; p=0.013). Regarding sAPP blood biomarker data, by study conclusion six subjects has pre- and post-acamprosate sAPP total and sAPPα levels available. In analysis of fractional change from baseline to endpoint, mean sAPP total levels reduced from 34.7 (ng/mL) at baseline to 19.3 at endpoint (p=0.02) and mean sAPPα levels reduced from 7.8 (ng/mL) at baseline to 4.2 at endpoint (p=0.03).

TABLE 5

Effects of Acamprosate on Youths Diagnosed with FXS linked ASD.

| Measure | Baseline Group Mean ± SD | Endpoint Group Mean ± SD | P value |
|---|---|---|---|
| CGI-S | 4.25 ± 0.45 | 3.33 ± 0.49 | <0.0001 |
| ABC Irritability | 9.9 ± 7.8 | 7.0 ± 8.9 | 0.106 |
| ABC Social Withdrawal | 7.33 ± 5.2 | 4.1 ± 6.5 | 0.014 |
| ABC Stereotypy | 6.8 ± 6.8 | 6 ± 6.3 | 0.085 |
| ABC Hyperactivity | 16.8 ± 9.1 | 11.0 ± 8.6 | 0.009 |
| ABC Inappropriate Speech | 5.2 ± 3.5 | 4.8 ± 3.4 | 0.605 |
| Social Responsiveness Scale (total raw score) | 91.3 ± 27.4 | 76.42 ± 26.8 | 0.005 |
| ADHD Rating Scale, 4$^{th}$ Edition | 23.6 ± 10.6 | 16.7 ± 8 | <0.0001 |
| PPVT | 85.2 ± 32 | 83.3 ± 32 | 0.53 |

TABLE 6

Summary of adverse effects observed in youths diagnosed with FXS linked ASD and treated with acamprosate.

| Adverse Effect | Number of Patients |
|---|---|
| Irritability (mild) | 4 |
| Increased repetitive behavior (mild) | 2 |
| Increased anxiety (mild) | 1 |
| Diarrhea (mild) | 1 |
| Constipation (mild) | 1 |
| Insomnia (mild) | 1 |
| Urinary urgency (mild) | 1 |
| Rhinitis (mild) | 1 |
| Nightmares (mild) | 1 |
| Increased body rocking (mild) | 1 |

Figure 2:
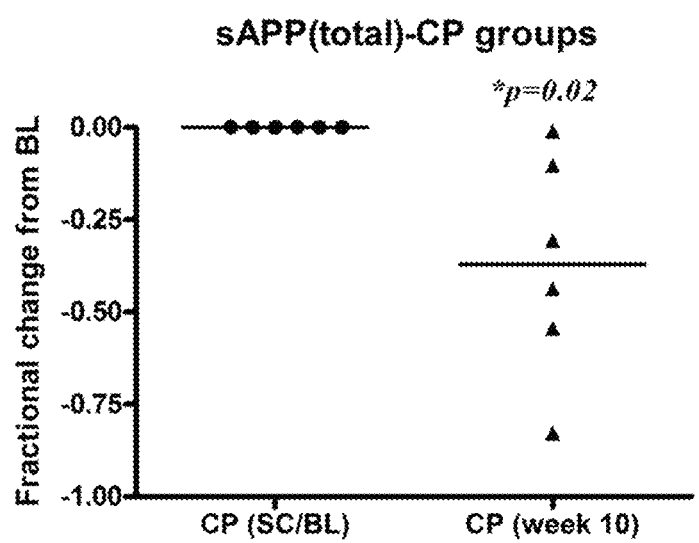
FIG. 2. Graph illustrating the relationship between the fractional change in sAPP(total)-CP levels measured in the blood of patients diagnosed with ASD and treated for 10 weeks with acamprosate.
Figure 3A:
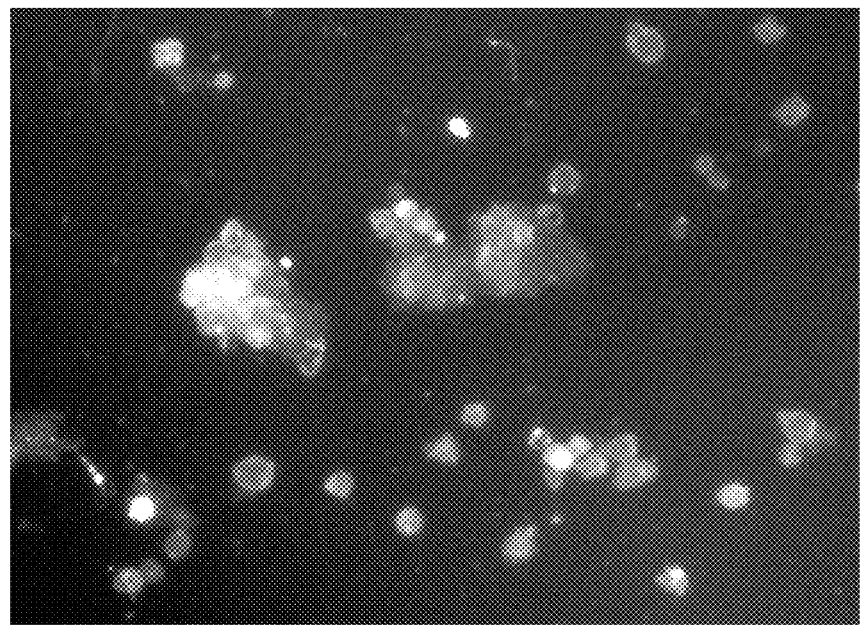
FIG. 3A. A photomicrograph of lymphocytes claimed onto a PDL-coated 24 well plate and treated with 10 mM tamoxifen (positive control).
Figure 3B:
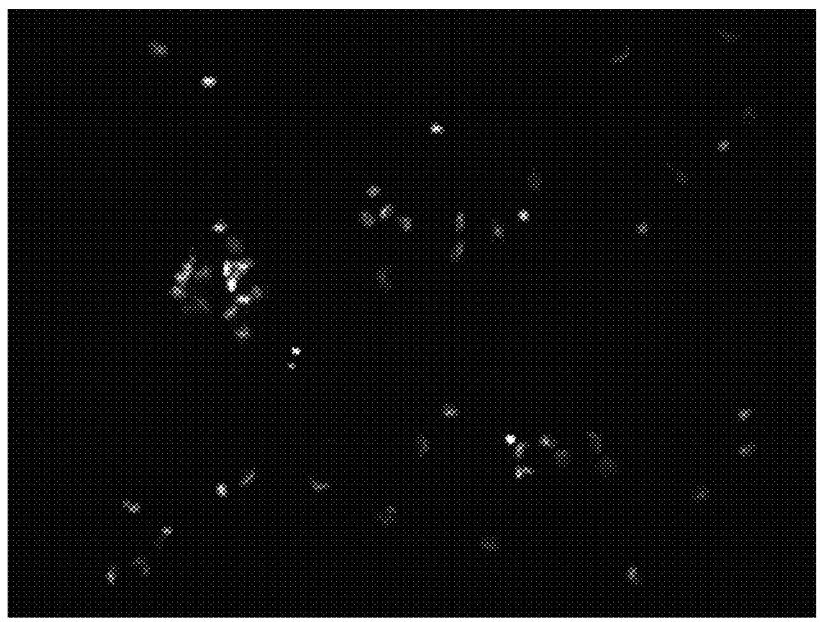
FIG. 3B. A photomicrograph of lymphocytes claimed onto a PDL-coated 24 well plate and treated with 10 mM tamoxifen nuclei stained by Hoechst stain.
Figure 3C:
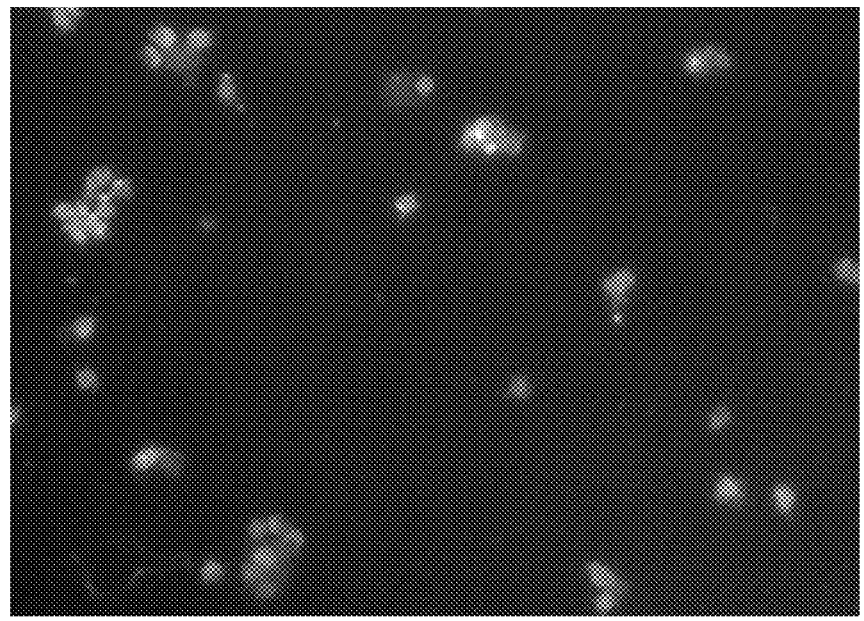
FIG. 3C. A photomicrograph of lymphocytes from untreated patient and stained with ERK/MAPK antibody; antibody shows 3 cells with cytosolic translocation of ERK/MAPK.
Figure 3D:
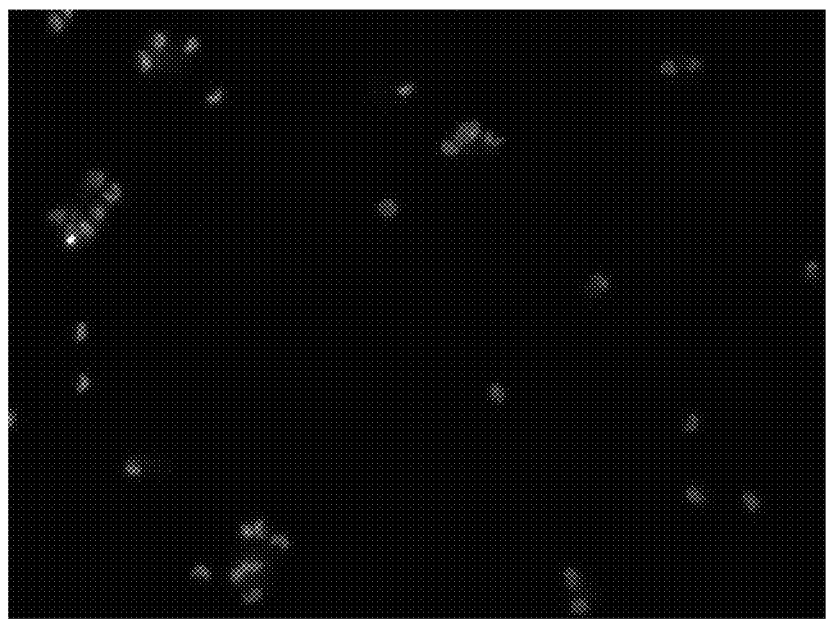
FIG. 3D. A photomicrograph of lymphocytes from FIG. 3C, showing the cells' nuclei.

Referring now to FIGS. 1 and 2. Graphs of the data in Tables 7 and 8, collected from 6 subjects with Fragile X Syndrome (FXS) who participated in the open label acamprosate trial. Peripheral blood sample were collected from 6 individual human patients. All 6 patients were diagnosed with FXS. Samples were drawn and analyzed before treatment with acamprosate and after treatment with acamprosate in order to measure the level of both sAPP total)—CP and sAPPα-CP in the samples. Levels of the specific proteins in the samples were determined by ELISA using the appropriate antibody.

The data presented in these graphs illustrate that treatment of patients with FXS with acamprosate is associated with normalizing (lowering) APP levels. This data shows that acamprosate may directly engage aberrant neuronal activity associated with FXS (in this case elevated APP). The level of APP in patents with FXS is a good clinical predictor of treatment response. Patients with the highest APP levels should be treated with acamprosate. Those patients who exhibit a reduction in APP during or after treatment with acamprosate should continue to be treated with the compound. APP levels can also be used as a screen for other compounds that may effective for the treatment of FXS. Compounds that lower APP levels may be useful for the treatment of FXS.

TABLE 7

Levels of sAPP(total)-CP measured in patients diagnosed
with FXS before and after treatment with Acamprosate.

| Patient | Lab# | Baseline | Lab#(Wk 12) | Week 12 | |
|---|---|---|---|---|---|
| 1 | 37 | 12.97575 | 46 | 12.84334 | −0.0102 |
| 2 | 39 | 9.003579 | 49 | 8.07674 | −0.10294 |
| 3 | 45 | 100.893 | 50 | 56.80199 | −0.43701 |
| 4 | 47 | 16.5507 | 51 | 7.547117 | −0.544 |
| 5 | 48 | 32.30696 | 53 | 5.561034 | −0.82787 |
| 6 | 52 | 36.27913 | 54 | 25.15706 | −0.30657 |

TABLE 8

Levels of sAPPα-CP measured in patients diagnosed
with FXS before and after treatment with Acamprosate.

| Patient | Lab# | Baseline | Lab#(Wk 12) | Week 12 | |
|---|---|---|---|---|---|
| 1 | 37 | 2.763889 | 46 | 2.763889 | 0 |
| 2 | 39 | 4.916667 | 49 | 4.777778 | −0.02825 |
| 3 | 45 | 18.38889 | 50 | 7.416667 | −0.59668 |
| 4 | 47 | 4.986111 | 51 | 2.694444 | −0.45961 |
| 5 | 48 | 8.597222 | 53 | 2.486111 | −0.71082 |
| 6 | 52 | 7.416667 | 54 | 5.055556 | −0.31835 |

This initial pilot placebo-controlled trial of acamprosate targeting social impairment in patients with FXS, demonstrated that the drug to be well tolerated with potential signs of efficacy noted specific to reductions in social deficits and hyperactivity. This study demonstrates that acamprosate use was associated with significant and uniform reductions in sAPP total and sAPPα pointing to a potential pharmacodynamics marker for the treatment of FXS.

In total, twenty-four youth (mean age 11.1 years; range 5-17 years) participated in these two pilot clinical trials.

Fifteen subjects had available pre- and post-acamprosate sAPP total and sAPPα assay data available. Post-treatment blood samples were not available from 3 subjects with FXS, 3 subjects with ASD were deemed placebo lead-in responders and did not receive acamprosate, and 3 subjects receiving acamprosate in the idiopathic ASD study were lost to follow-up during active acamprosate treatment and did not complete post-treatment blood analysis. Using pre-specified indicators of clinical response, 9 of 12 youth with FXS and 6 of 9 youth with idiopathic ASD were judged responders to acamprosate. Generally, clinical improvement was noted in social behavior and inattention/hyperactivity. Pooled subject mean IQ was 56 (range 36 to 96). Pooled subject final acamprosate dosing was 1,054 mg/day. Overall, sAPP total reduced with use of acamprosate from a mean 32.6±38.3 ng/mL pre-treatment to 21.4±32.3 ng/mL post-treatment (p=0.01). sAPPα reduced with use of acamprosate from a mean 8.4±7.9 ng/mL pre-treatment to 5.5±7.2 ng/mL post-treatment (p=0.003). Levels of both sAPP total and sAPPα reduced with treatment in every sample tested except in one subject with idiopathic ASD where sAPPα was unchanged following treatment. No significant correlations between percent change in sAPP total or sAPPα and percent change in scores on the ABC-SW were noted in the pooled 15 subject sample. Within the 9 subject subset of those with FXS, a significant correlation was noted between change in sAPP total and ABC-SW scores meaning that more reduction in sAPP total correlated with greater improvement in ABC-SW scores (Spearman Correlation Coefficient=0.853; p=0.003).

ERK12 Activity Measured in Mice

A summary of data collected using mouse models for ASD to measure the effect of acamprosate on the levels of ERK activity in wild-type and fmr1 (fragile X gene) Knock Out mice.

| WT Saline | training left | training right | Total | P.I. | average | test novel | test fam | total |
|---|---|---|---|---|---|---|---|---|
| 3-1 | 33.78 | 30.22 | 64 | 0.055625 | 0.193298 | 40.74 | 40.55 | 81.29 |
| 3-2 | 54.89 | 34.27 | 89.16 | 0.23127 | | 43.03 | 24.99 | 68.02 |
| 2-1 | 86.75 | 37.35 | 124.1 | 0.398066 | | 63.37 | 27.41 | 90.78 |
| 2-2 | 90.77 | 77.66 | 168.43 | 0.077836 | | 37.13 | 28.38 | 65.51 |
| 3-1 | 66.74 | 37.14 | 103.88 | 0.284944 | | | | |
| 3-2 | 98.56 | 72.67 | 171.23 | 0.1512 | | 35.56 | 46.44 | 82 |
| 3-3 | 49.08 | 35.97 | 85.05 | 0.154145 | | 45.89 | 22.69 | 68.58 |
| KO Saline | | | | | | | | |
| 2-1 | 79.58 | 72.21 | 151.79 | 0.048554 | 0.022521 | 27.19 | 47.84 | 75.03 |
| 2-2 | 36.7 | 34.87 | 71.57 | 0.025569 | | 49.26 | 16.05 | 65.31 |
| 1-1 | 39.45 | 51.55 | 91 | −0.13297 | | 80.6 | 29.91 | 110.51 |
| 1-2 | 97.91 | 45.69 | 143.6 | 0.363649 | | 55.38 | 55.41 | 110.79 |
| 1-1 | 55.3 | 49.25 | 104.55 | 0.057867 | | 62.08 | 51.53 | 113.61 |
| 1-2 | 42.96 | 68.27 | 111.23 | −0.22755 | | 37.48 | 35.69 | 73.17 |
| KO Acam | | | | | | | | |
| 1-1 | 52.72 | 36.55 | 89.27 | 0.181136 | 0.06358 | 47.09 | 24.3 | 71.39 |
| 1-2 | 75.63 | 60.11 | 135.74 | 0.114336 | | 64.3 | 40.3 | 104.6 |
| 3-1 | 44.92 | 37.52 | 82.44 | 0.089762 | | 91.23 | 28.38 | 119.61 |
| 3-2 | 43.53 | 53.74 | 97.27 | −0.10497 | | 50.11 | 28.7 | 78.81 |
| 2-1 | 45.98 | 32.97 | 78.95 | 0.164788 | | 60.28 | 32.28 | 92.56 |
| 2-2 | 70.91 | 88.22 | 159.13 | −0.10878 | | 37.69 | 47.59 | 85.28 |
| 2-3 | 88.22 | 70.91 | 159.13 | 0.108779 | | 62.2 | 30.2 | 92.4 |
| P.I. | average | | | | mean | STD | SEM | |
| 0.002337 | 0.1671419 | | WT Sal | train | 0.193298 | 0.120666 | 0.04562 | |
| 0.265216 | | | | test | 0.167142 | 0.204707 | 0.083588 | |
| 0.396122 | | | | | | | | |
| 0.133567 | | | KO Sal | train | 0.022521 | 0.202492 | 0.082684 | |
| | | | | test | 0.134837 | 0.298279 | 0.121796 | |

-continued

| WT Saline | training left | training right | Total | P.I. | average | test novel | test fam | total |
|---|---|---|---|---|---|---|---|---|
| −0.13268 0.338291 | | | KO Acam | train | 0.06358 | 0.120749 | 0.045652 | |
| | | | | test | 0.268363 | 0.19376 | 0.073255 | |
| P.I. −0.27522 0.508498 0.458692 | average 0.1348368 | | STD SE | | 0.120666 0.04562 | training WT sal | | |
| −0.00027 0.092862 0.024464 | | | STD SE | | 0.204707 0.083588 | test WT sal | | |
| P.I. 0.319232 0.229446 0.525458 0.271666 0.302506 −0.11609 0.34632 | average 0.2683629 | | STD SE | | 0.202492 0.082684 | training KO sal | | |
| | | | STD SE | | 0.298279 0.121796 | test KO sal | | |
| | | | STD SE | | 0.120749 0.045652 | training KO Acam | | |
| | | | STD SE | | 0.19376 0.073255 | Test KO Acam | | |

Figure 4:
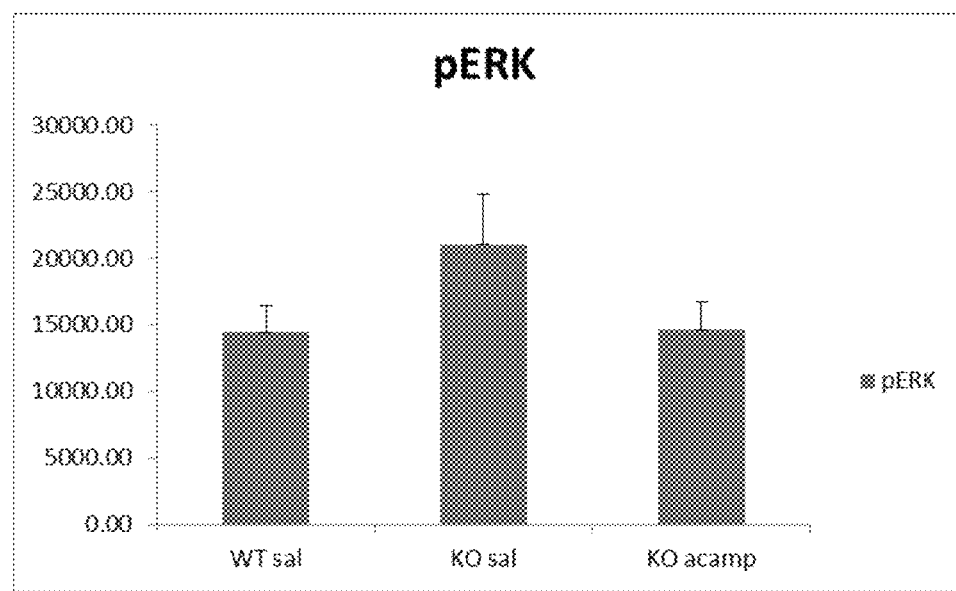
FIG. 4. Bar graph of pERK activity measured in WT and fmr1 KO mice treated with acamprosate

Referring now to FIG. 4. A summary of data collected using mouse models for ASD to measure the effect of acamprosate on the levels of ERK activity in wild-type and fmr1 (fragile X gene) Knock Out mice.

| STRIATUM | | | | | A = ERK/ |
|---|---|---|---|---|---|
| | pERK | ERK | Total | Total | pERK/A |
| WT sal | 12699 | 18941 | 14124 | 1.34 | 9469.44 |
| WT sal | 20715 | 17474 | 13395 | 1.30 | 15879.45 |
| WT sal | 22351 | 26513 | 20378 | 1.30 | 17179.07 |
| WT sal | 21796 | 20806 | 20223 | 1.03 | 21185.26 |
| WT sal | 13097 | 32261 | 15652 | 2.06 | 6354.24 |
| WT sal | 29173 | 31531 | 19994 | 1.58 | 18498.78 |
| WT sal | 17884 | 29104 | 20538 | 1.42 | 12620.31 |
| KO sal | 30552 | 17568 | 14140 | 1.24 | 24590.46 |
| KO sal | 19226 | 21575 | 14967 | 1.44 | 13337.45 |
| KO sal | 24898 | 17972 | 20766 | 0.87 | 28768.74 |
| KO sal | 34884 | 22150 | 22320 | 0.99 | 35151.73 |
| KO sal | 24677 | 35094 | 19275 | 1.82 | 13553.58 |
| KO sal | 17069 | 31301 | 19971 | 1.57 | 10890.55 |
| KO Acam | 26311 | 24161 | 18506 | 1.31 | 20152.78 |
| KO Acam | 37905 | 32570 | 20784 | 1.57 | 24188.44 |
| KO Acam | 34961 | 26811 | 9659 | 2.78 | 12595.14 |
| KO Acam | 25699 | 27464 | 11290 | 2.43 | 10564.44 |
| KO Acam | 25451 | 25163 | 11468 | 2.19 | 11599.26 |
| KO Acam | 19381 | 21441 | 9535 | 2.25 | 8618.90 |
| KO Acam | 25020 | 25808 | 15062 | 1.71 | 14602.11 |
| | WT sal | KO sal | KO acamp | | |
| | 9469.44 | 24590.46 | 20152.78 | | |
| | 15879.45 | 13337.45 | 24188.44 | | |
| | 17179.07 | 28768.74 | 12595.14 | | |
| | 21185.26 | 35151.73 | 10564.44 | | |
| | 6354.24 | 13553.58 | 11599.26 | | |
| | 18498.78 | 10890.55 | 8618.90 | | |
| | 12620.31 | | 14602.11 | | |
| | WT sal | KO sal | KO acamp | | |
| pERK | 14455.22 | 21048.75 | 14617.30 | | |
| SEM | 1981.72 | 3741.15 | 2114.87 | | |
| T Test | | 0.18 | 0.96 | 0.20 | |
| | | WT vs KO sal | WT vs KO acamp | KO sal vs KO acamp | |

ERK/2 Activity Measured in Humans by Western Blotting

Just after drawing the blood and isolating mononuclear cells by Western immunoblotting. Whole blood samples were obtained from the Riley Autism Clinic. Lymphocytes were isolated from blood by centrifuging samples in BD Vacutainer CPT tubes at 2800 RPM for 20 minutes. After centrifugation, lymphocyte layer was transferred to a fresh 15-ml conical tube and centrifuged at 1300 RPM for 15 minutes. Supernatant was aspirated and the pellet was resuspended in 1 ml 1×PBS. The samples were again centrifuged at 1300 RPM for 10 minutes. Supernatant was aspirated and pellet resuspended slowly in 500 µl RPMI 1640 containing 10% FBS. After using cells to plate, the remaining cells were transferred to an Eppendorf tube and centrifuged at 400×g for 6 minutes. Supernatant was removed and the pellet was used to make cell lysate.

The total protein from cell lysates was measured using the Bradford protein assay. Volumes were calculated to load 10 µg in each lane of a 15-lane gel. Laemmli Sample Buffer and water were used to bring each sample up to 30 µl total. Samples were denatured at 95° for 5 minutes using a thermo cycler. Running buffer was added to a cassette before loading wells with sample. Protein standard was loaded in one lane as a marker. Human fetal neuron (HFN) lysate and human brain lysate were also loaded to serve as controls. Gel was run at 200V for 1 hour.

Transfer was performed using the Invitrogen iBlot system. Dry transfer was performed for 7 minutes and the PVDF blot was Ponceau stained for 10 minutes to observe protein transfer afterwards. After staining, the blot was rinsed in TBST to neutralize the acidic nature of the Ponceau stain. Blocking was performed with 5% milk in TBST for 1 hour. This was discarded and the blot was probed with phospho-ERK primary antibody diluted in 5% milk in TBST overnight at 4° C. The following day, primary antibody was removed, and the blot was washed in TBST 3 times for 10-minutes each. The blot was placed in goat-anti-rabbit secondary antibody diluted in 5% milk in TBST for one hour. The blot was then rinsed in TBST 3 times for minutes each.

After rinsing, 1:1 Enhanced Chemiluminescence (ECL) reagent was added to the PDVF membrane and incubated at room temperature for 1 minute. Film was developed at 15-minutes and 25-minutes. Blot was stripped for 8 minutes, then rinsed in TBST for 5 minutes. The blot was then blocked in 5% milk in TBST for 1 hour and reprobed with pan-ERK (1:1000) primary antibody overnight at 4° C.

Goat-anti-rabbit was also used at the secondary antibody in this case. Blot was rinsed and film was developed as previously described. Gel densitometry was performed using ImageJ software. A phospho-to-pan-ERK ratio was determined and plotted using Prism software.

Lymphocytes and ICC of Fixed Mononuclear Cells for ERK/MAPK Activity (Anti-Phospho-Thr202/Tyr204 ERK/MAPK)

Lymphocyte samples were prepared from patient's blood and plated onto a PDL-coated 24-well plate. Cells were fixed by adding 4% paraformaldehyde in PB solution (at RT). Excess paraformaldehyde solution was aspirate out. The fixed cells were washed three times gently with cold DPBS (Bulbecco-modified phosphate buffered saline). Then 0.12% Triton X-100 (diluted in DPBS) was added onto the cells at RT and incubated for 20 minutes at RT. Excess Triton X solution was aspirated out and cells were washed three times (gently) with chilled DPBS. Cells were blocked with 10% horse serum (HS) (diluted in DPBS) for 20 minutes at RT. Unbound blocking agent was washed off. The primary antibody diluted in 1% HS in DPBS was added. Generally a dilution of 1:250 was used. The antibody, which is raised in rabbit recognizes Phospho-Thr202/Tyr204 of ERK/MAPK, which indicates translocation of activated ERK/MAPK into the cytosolic compartment.

Incubation with the primary antibody was done for overnight at 4° C. Unbound primary antibody was washed off, and at this stage the plate can be stored at 4° C. Washed three times at RT with cold DPBS. Added Alexa Fluor conjugated goat anti rabbit (diluted 1:200 in DPBS) and incubated at RT for 1-2 hr. This reagent and this step is light sensitive to. For best results the reagent and this step of the procedure should be kept away from the light. Turned off the light of the room and aspirated out the secondary antibody and discard. Again, washed three times with DPBS at RT. DPBS was taken in a 15 mL tube and Hoechst stain (1:500 dilution) was added in that. The diluted Hoechst stain containing solution was added into each well.

The picture was taken under the microscope in dark using specific filters for Hoechst and Alexa Fluor (the capture time of the camera has to be manually setup and use the same capture time for every image).

Positive Controls: Cells were treated with 10 M tamoxifen, which served as a positive control. Tamoxifen induces ERK activation and translocation of ERK/MAPK was observed in the cytosolic compartment of the cells. Further, bright nuclei were stained by Hoechst.

An analysis of data on basal ERK1/2 activation in peripheral lymphocytes from 37 youths ages 5-17 years of age and diagnosed with idiopathic ASD (mean ages 10.1 years) versus 13 age and gender matched neurotypical control subjects (mean age of 10.4 years). Youths with ASD had means basal ERK/2 activation of 7.1+7.1% versus an activation ration of 2.8+2.1% in control subject (p=0.01)' Cohen's d=0.82. Enhanced ERK1/2 activation in youths with ASD was also confirmed by Western Blot Analysis (data not shown).

The glutamatergic agent riluzole modifies ERK1/2 activation rates in adults with FXS. Experiments with fmr1 animals demonstrates that acamprosate use in the fmr1 knockout animals rescues excessive baseline elevation in ERK activation i. e. acamprosate restores activated ERK to wild-type levels. These results demonstrate and that acamprosate restores enhanced ERK1/2 activation to wild-type levels in a mouse model of FXS. These results show that ERK1/2 is a drugable target in humans diagnosed ADS and related neurological disorders. These results also demonstrate that ERK activation can be used as biomarker in the use of acamprosate to treat and/or to study fragile X and fragile X like diseases in humans. Abnormal levels of ERK1/2 activation are observed in patients with ASD and in a mouse models for this condition. The observation that the treating mice models FXS with acamprosate changes the rate of ERK1/2 activation argues that acamprosate will help to return to levels of ERK1/2 activity in ASD to the levels of ASD activity in matched subjects that do not exhibit ASD.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method of screening for a compound, comprising the steps of:
    contacting a first sample of plasma from a patient characterized as having autism spectrum disorder (ASD) under ADOS or exhibiting a lack of fragile X mental retardation protein (FMRP) with a first reagent that selectively binds to activated ERK 1/2 and one or more reagents selected from the group consisting of: a reagent that selectively binds to BDNF, a reagent that selectively binds to sAPP, and a reagent that binds to sAPPα;
    determining the level of activated ERK 1/2 in the first sample of plasma;
    determining the level of at least one BDNF, sAPP, and sAPPα in the first sample of plasma;
    administering at least one compound to the patient;
    contacting a second sample of plasma from the patient with the first reagent that selectively binds to activated ERK 1/2 and the one or more of the reagents that selectively binds to BDNF, sAPP, and sAPPα;
    determining the level of activated ERK 1/2 in the second sample of plasma;
    determining the levels of at least one BDNF, sAPP, and sAPPα in the second sample of plasma; and
    selecting a compound if that compound causes a change in the level of activated ERK 1/2 determined in the second sample of plasma relative to the level of activated ERK1 or ERK2 determined in the first sample of plasma and causes a change in the level of at least one of BDNF, sAPP, and sAPPα in the second sample of plasma relative to the levels of at least one of BDNF, sAPP, and sAPPα in the first sample of plasma, wherein the compounds may be useful in the treatment of idiopathic or FXS-linked ASD.

2. The method of claim 1, wherein the selected reagent comprises an antibody that selectively binds to BDNF.

3. The method of claim 1, wherein the selected reagent comprises an antibody that selectively binds to sAPP.

4. The method of claim 1, wherein the selected reagent comprises an antibody that selectively binds to sAPPα.

5. The method of claim 1, further including the step of:

assessing if a change caused by the compound includes at least one change selected from the group consisting of: a change in the level of BDNF, a change in the level of sAPP, a change in the level of activated ERK 1, a change in the level of activated ERK 2, and a decrease in the level of sAPPα.

6. The method of claim 1, further including the step of: altering the amount of the compound administered to the patient.

7. The method of claim 1, wherein the patient is a human or a mammalian model for idiopathic ASD or FXS.

\* \* \* \* \*